US010583710B2

(12) United States Patent
McQuillen et al.

(10) Patent No.: US 10,583,710 B2
(45) Date of Patent: Mar. 10, 2020

(54) SYSTEMS AND METHODS FOR CALIBRATING VEHICLE SENSING DEVICES

(71) Applicant: Ford Global Technologies, LLC, Dearborn, MI (US)

(72) Inventors: Michael McQuillen, Warren, MI (US); Daniel A. Makled, Dearborn, MI (US); Gopichandra Surnilla, West Bloomfield, MI (US); Richard E. Soltis, Saline, MI (US); Radhakrishnan Swaminathan, Grand Blanc, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 113 days.

(21) Appl. No.: 15/588,140

(22) Filed: May 5, 2017

(65) Prior Publication Data
US 2018/0319250 A1 Nov. 8, 2018

(51) Int. Cl.
*B60H 1/00* (2006.01)
*B60H 1/12* (2006.01)
(Continued)

(52) U.S. Cl.
CPC ..... *B60H 1/00785* (2013.01); *B60H 1/00828* (2013.01); *B60H 1/00978* (2013.01);
(Continued)

(58) Field of Classification Search
CPC .. B60H 1/00785; B60H 1/00828; B60H 1/12; B60H 1/00978; B60H 1/3205;
(Continued)

(56) References Cited

U.S. PATENT DOCUMENTS 6,230,543 B1 * 5/2001 Froehling ............ G01N 27/223
73/1.06
8,081,539 B2 12/2011 Faber et al.
(Continued)

FOREIGN PATENT DOCUMENTS

CN 203504610 U 3/2014
CN 104684112 A 6/2015
(Continued)

OTHER PUBLICATIONS

McQuillen, M. et al., "Systems and Methods for Humidity Determination and Uses Thereof," U.S. Appl. No. 15/286,211, filed Oct. 5, 2016, 115 pages.
(Continued)

*Primary Examiner* — Henry T Crenshaw
(74) *Attorney, Agent, or Firm* — Geoffrey Brumbaugh; McCoy Russell LLP

(57) ABSTRACT

Methods and systems are provided for improving operation of a vehicle heating, ventilation, and air conditioning system. In one example, a method may include calibrating a vehicle humidity sensor position inside a cabin of the vehicle by obtaining one or more humidity measurements with one or more personal computing devices positioned inside the cabin, and may further include adjusting operation of the heating, ventilation, and air conditioning system responsive to the calibration. In this way, an interior humidity sensor of a vehicle may be regularly calibrated, which may improve operation of the vehicle heating, ventilation, and air conditioning system, and may further increase fuel economy.

19 Claims, 15 Drawing Sheets

(51) Int. Cl.
*B60H 1/32* (2006.01)
*G01N 33/00* (2006.01)
*G01N 27/22* (2006.01)

(52) U.S. Cl.
CPC ............ *B60H 1/12* (2013.01); *B60H 1/3205* (2013.01); *B60Y 2200/92* (2013.01); *G01N 27/223* (2013.01); *G01N 33/0006* (2013.01)

(58) Field of Classification Search
CPC .. B60Y 2200/92; G01K 15/007; G01K 13/00; G01W 1/14; G01N 27/048; G01L 9/00; G07C 5/0841; G07C 5/0808; G07C 5/008
See application file for complete search history.

(56) References Cited

U.S. PATENT DOCUMENTS

| | | | |
|---|---|---|---|
| 8,140,215 B2* | 3/2012 | Paquette | H04L 67/12 340/901 |
| 8,315,759 B2 | 11/2012 | Bauerle | |
| 9,462,319 B2 | 10/2016 | Bai et al. | |
| 2003/0152088 A1* | 8/2003 | Kominami | B60N 2/0248 370/401 |
| 2005/0253912 A1* | 11/2005 | Smith | B41J 2/04553 347/102 |
| 2007/0139216 A1* | 6/2007 | Breed | G08C 17/00 340/13.24 |
| 2008/0189009 A1 | 8/2008 | Wang et al. | |
| 2010/0188932 A1* | 7/2010 | Hanks | G01S 7/52004 367/140 |
| 2012/0231841 A1* | 9/2012 | Niederberger | H04M 1/21 455/556.1 |
| 2013/0255605 A1* | 10/2013 | Jentz | F01P 11/16 123/41.15 |
| 2013/0261808 A1* | 10/2013 | Besore | G05D 23/1904 700/278 |
| 2014/0004782 A1* | 1/2014 | Maranville | B60H 1/26 454/75 |
| 2015/0161830 A1* | 6/2015 | Lenhardt | G01K 13/00 701/30.5 |
| 2016/0189362 A1* | 6/2016 | Evers-Senne | G06T 7/70 348/46 |
| 2017/0096048 A1* | 4/2017 | Larson | B60H 1/3207 |
| 2017/0135159 A1* | 5/2017 | Sorenson | A47J 37/0611 |
| 2017/0234564 A1* | 8/2017 | Goel | F24F 11/77 62/93 |
| 2018/0130267 A1* | 5/2018 | Jones | G07C 5/008 |
| 2018/0141567 A1* | 5/2018 | Surnilla | B60W 50/0225 |

FOREIGN PATENT DOCUMENTS

| | | |
|---|---|---|
| CN | 205028572 U | 2/2016 |
| JP | H11304911 A | 11/1999 |

OTHER PUBLICATIONS

McQuillen, M. et al., "Systems and Methods for Humidity Determination and Uses Thereof," U.S. Appl. No. 15/286,277, filed Oct. 5, 2016, 117 pages.

McQuillen, M. et al., "Systems and Methods for Humidity Determination and Uses Thereof," U.S. Appl. No. 15/286,318, filed Oct. 5, 2016, 116 pages.

Surnilla, G. et al., "Vehicle Sensor Calibration Using Wireless Network-Connected Sensors," U.S. Appl. No. 15/356,143, filed Nov. 18, 2016, 24 pages.

McQuillen, M. et al., "Systems and Methods for Calibrating Vehicle Sensing Devices," U.S. Appl. No. 15/588,216, filed May 5, 2017, 109 pages.

McQuillen, M. et al., "Systems and Methods for Calibrating Vehicle Sensing Devices," U.S. Appl. No. 15/588,296, filed May 5, 2017, 107 pages.

* cited by examiner

FIG. 7

| IoT Weather device source | Confidence level in IoT measurement based on source |
|---|---|
| End of line calibration | High |
| Dealership (same as make of vehicle) | High |
| Personal home | Medium |
| IoT enabled facility (e.g. dealership that differs from make of vehicle, a friend's house, etc. | Low |
| Crowdsourced | Confidence-based |

| IoT data source | Confidence level | Exterior humidity, intake humidity, OAT, BP sensors | Ultrasonic sensor | Engine | Oxygen sensor |
|---|---|---|---|---|---|
| End of line calibration | High | Compensate sensor reading when sensor reading is beyond a first threshold from IoT reading | Utilize IoT data for ultrasonic sensor compensation (e.g. compensation for attenuation changes, speed of sound changes) | Utilize IoT data for improved engine operation (e.g. increased fuel economy) | Utilize IoT data to apply a gain correction to the UEGO sensor output |

FIG. 9

| IoT data source | Confidence level | Exterior humidity, intake humidity, OAT, BP sensors | Ultrasonic sensor | Engine | UEGO |
|---|---|---|---|---|---|
| Dealer-Ship | High | Compensate sensor when sensor reading is beyond a first threshold from IoT reading | Utilize IoT data for ultrasonic sensor compensation (e.g. compensation for attenuation changes, speed of sound changes) | Utilize IoT data for improved engine operation (e.g. increased fuel economy) | Utilize IoT data to apply a gain correction to the UEGO sensor output |

FIG. 10

| IoT data source | Confidence level | Exterior humidity, intake humidity, OAT, BP sensors | Ultrasonic sensor | Engine | UEGO |
|---|---|---|---|---|---|
| Personal home | Medium | Compensate sensor when sensor reading is beyond a second threshold from IoT reading | Ignore home device if a threshold duration has passed since a higher confidence measurement, or if repeated measurements from medium confidence IoT devices result in a degraded confidence in IoT measurement | Ignore home device if a threshold duration has passed since a higher confidence measurement from IoT device, or if repeated measurements from medium confidence IoT devices result in a degraded confidence in IoT measurement | Ignore home device if a threshold duration has passed since a higher confidence measurement, or if repeated measurements from medium confidence IoT devices result in a degraded confidence in IoT measurement |

FIG. 11

| IoT data source | Confidence level | Exterior humidity, intake humidity, OAT, BP sensors | Ultrasonic sensor | Engine | UEGO |
|---|---|---|---|---|---|
| IoT enabled facility | Low | Compensate sensor when sensor reading is beyond a third threshold from IoT reading | Ignore IoT data | Ignore IoT data | Ignore IoT data |

FIG. 12

| IoT data source | Confidence level | Exterior humidity, intake humidity, OAT, BP sensors | Ultrasonic sensor | Engine | UEGO |
|---|---|---|---|---|---|
| Crowd-sourced | Confidence based | Perform compensation only if crowdsourced algorithm yields a high confidence result | Utilize IoT data for accurate ultrasonics control responsive to high confidence crowdsource data | Utilize IoT data for accurate engine control responsive to high confidence crowdsource data | Utilize IoT data for accurate UEGO control responsive to high confidence crowdsource data |

SYSTEMS AND METHODS FOR CALIBRATING VEHICLE SENSING DEVICES

FIELD

The present description relates generally to methods and systems for compensating one or more sensors onboard a vehicle, and adjusting one or more vehicle operating parameters in response to the compensated one or more sensors.

BACKGROUND/SUMMARY

A goal of automotive heating, ventilating, and air conditioning (HVAC) systems is to make vehicle occupants comfortable. To achieve this goal, it may be important that the design of the control system that establishes cabin conditions takes into account the relationship between comfort and the variables that affect comfort.

In an attempt to measure and control the many variables that affect comfort, modern automotive HVAC systems have a numerous sensors and control actuators. An HVAC system may have a temperature sensor inside the cabin, one measuring ambient temperature outside, and others measuring various temperatures of the systems' internal workings. A vehicle occupant may have an ability to provide some input to the HVAC system via a set point, or adjustment. Additional sensors measuring sun heating load, humidity, etc., may be available to the HVAC system. A set of actuators may include a variable speed blower, some means for varying air temperature, ducting, and vents to control the direction of air flow and the ratio of fresh air to recirculated air.

In some examples, a vehicle may include an interior cabin humidity sensor, which may comprise a dielectric or capacitive humidity sensor. In such an example, the interior cabin humidity sensor's readings may be affected by localized humidity in the air immediately surrounding the sensor. Such a sensor may be difficult to rationalize, or calibrate, as humidity inside a cabin of the vehicle may be substantially different than humidity external to, or surrounding the vehicle. An interior cabin humidity sensor that is not regularly calibrated, or compensated, may adversely affect the HVAC system, and its ability to regulate comfort level, fog inside the vehicle cabin on the vehicle windows, etc. Thus, a method for regularly calibrating an interior humidity sensor positioned in a cabin of a vehicle, is desired.

The inventors herein have recognized these issues, and have developed systems and methods to at least partially address the above issues. In one example, the issues described above may be addressed by a method comprising calibrating a first vehicle humidity sensor positioned inside a cabin of a vehicle via obtaining one or more humidity measurements with one or more personal computing devices positioned inside the cabin; and adjusting a vehicle heating, ventilation, and air conditioning (HVAC) system responsive to calibrating the first vehicle humidity sensor. In one example, the one or more personal devices includes a second humidity sensor, and in some examples, the one or more personal computing devices comprises a cellular phone. In this way, a vehicle's interior humidity sensor may be calibrated via a sensor experiencing the same environment as the interior humidity sensor.

As an example obtaining the one or more humidity measurements with the one or more personal computing devices further comprises positioning the one or more personal computing devices within a threshold distance from the first humidity sensor prior to obtaining the one or more humidity measurements. For example, positioning the one or more personal computing devices within the threshold distance from the first humidity sensor may in some examples include using one or more cameras included in the one or more personal computing devices to direct the one or more personal computing devices to within the threshold distance. In some examples, the one or more personal computing devices are equipped with a software application, the software application including instructions pertaining to how to obtain the one or more humidity measurements. In this way, accurate humidity measurements for calibrating a vehicle's interior humidity sensor may be obtained via the use of the personal computing device, which may be more accurate for calibrating an interior humidity sensor than relying on humidity information stemming from external to a cabin of the vehicle.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 7 depicts an example lookup table for determining a confidence level of an IoT weather device data source.

FIG. 8 depicts an example lookup table for determining one or more sensor(s) to compensate and one or more vehicle operating parameters to update based on an IoT data source comprising an end of line calibration.

FIG. 9 depicts an example lookup table for determining one or more sensor(s) to compensate and one or more vehicle operating parameters to update based on an IoT data source comprising a dealership of the same make as the vehicle receiving said data.

FIG. 10 depicts an example lookup table for determining one or more sensor(s) to compensate and one or more vehicle operating parameters to update based on an IoT data source comprising a home of the owner of the vehicle receiving said data.

FIG. 11 depicts an example lookup table for determining one or more sensor(s) to compensate and one or more vehicle operating parameters to update based on an IoT data source comprising an IoT-enabled facility.

FIG. 12 depicts an example lookup table for determining one or more sensor(s) to compensate and one or more vehicle operating parameters to update based on crowd-sourced IoT data.

DETAILED DESCRIPTION

Figure 2:
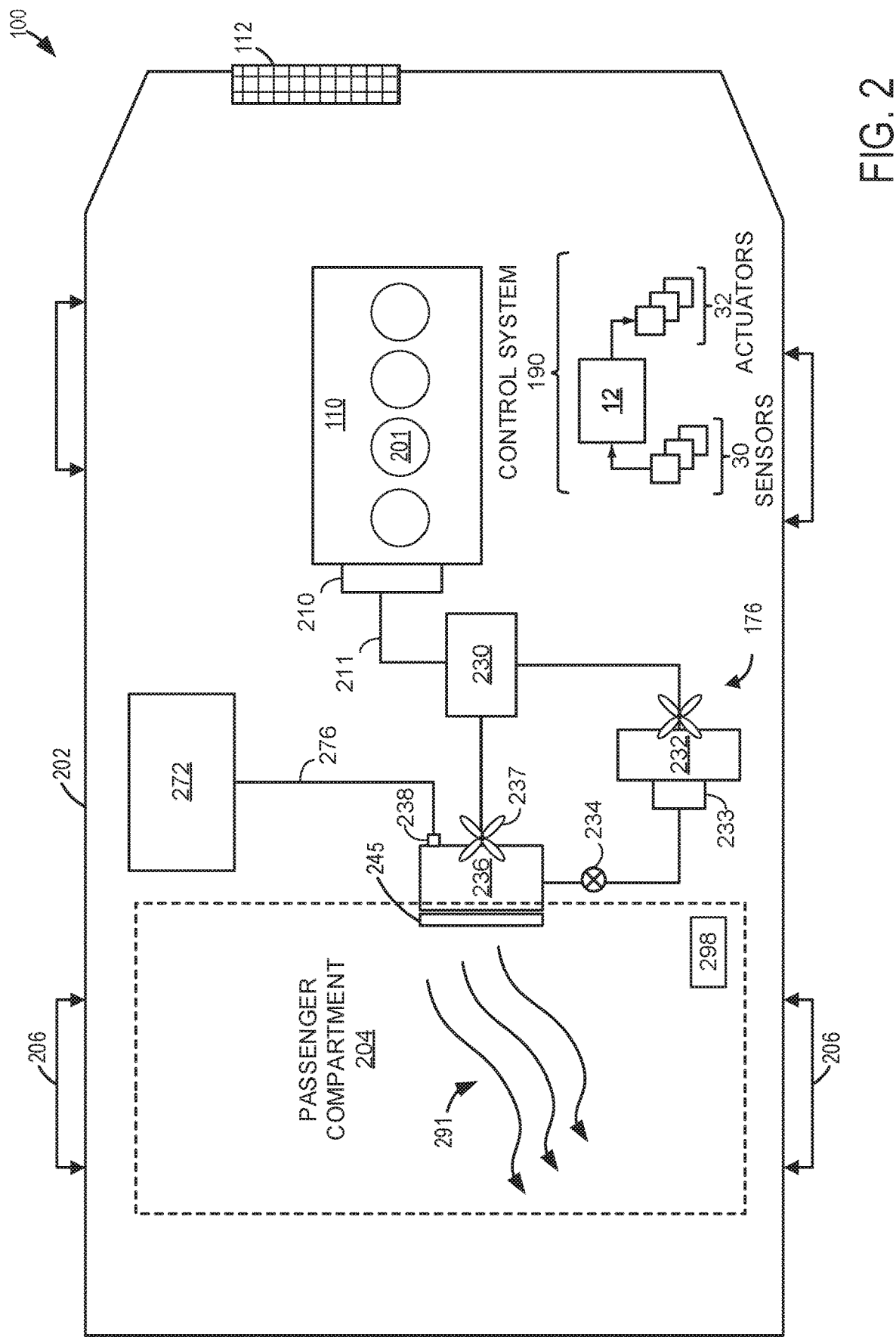
FIG. 2 shows a schematic diagram of a vehicle system including an air conditioning system, and an engine.
Figure 3:
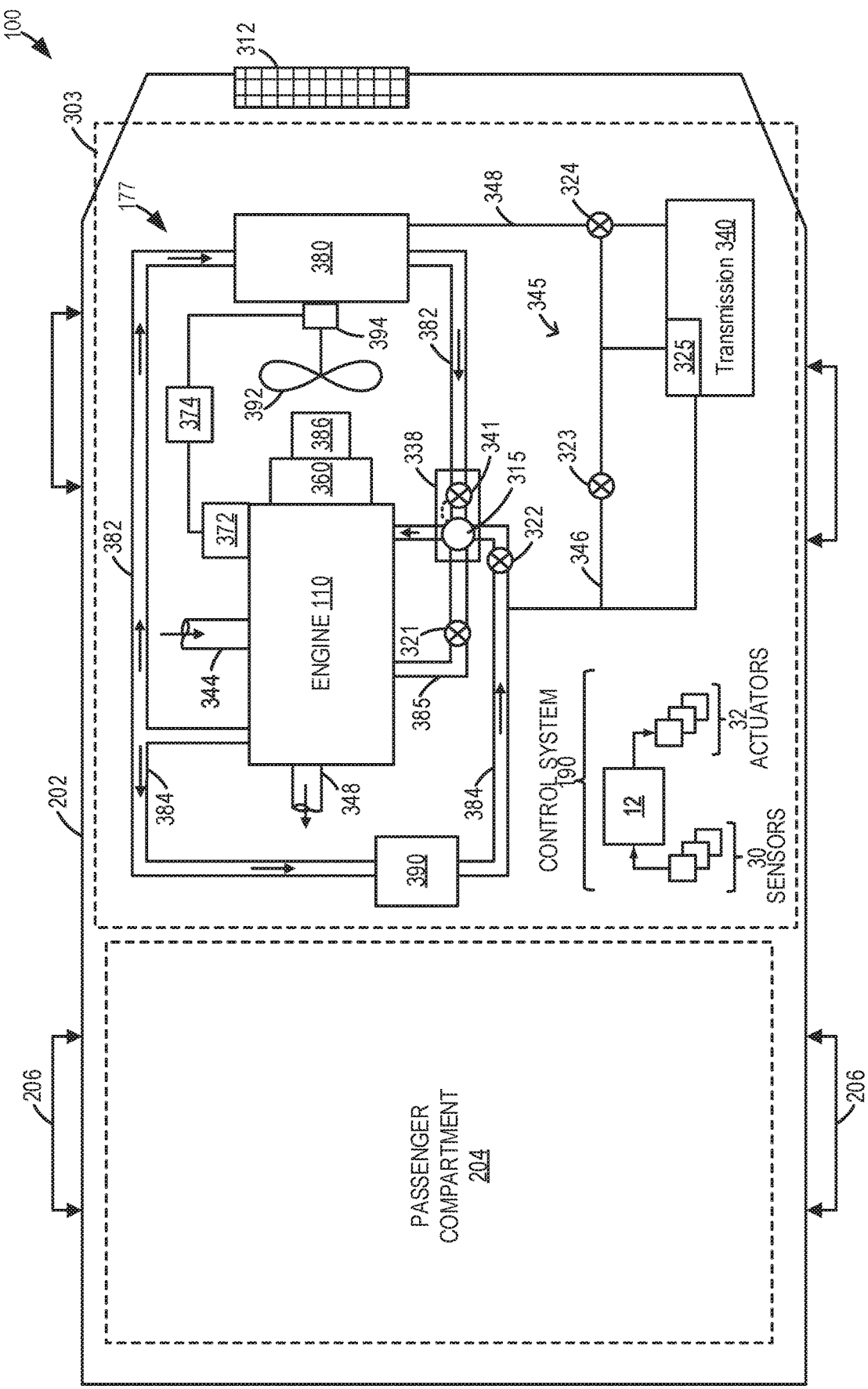
FIG. 3 shows a schematic diagram of a vehicle system including a cooling system according to an embodiment of the present disclosure.

The following description relates to systems and methods for calibrating various vehicle sensors, and, in some examples, for adjusting various vehicle operating parameters responsive to the calibration of various vehicle sensors. In some examples, the vehicle may comprise a hybrid vehicle system, such as the example vehicle propulsion system depicted in FIG. 1. However, in other examples, the vehicle system may not comprise a hybrid vehicle system, without departing from the scope of the present disclosure. In some examples, various aspects of a vehicle heating, ventilation, and air-conditioning system may be adjusted responsive to calibration of one or more sensors. FIG. 2 illustrates relevant aspects of an air-conditioning system, while FIG. 3 illustrates relevant aspects of a vehicle cooling system including a heater core for transferring heated air to a cabin of the a vehicle. In other examples, various aspects of a vehicle engine system, such as the engine system, depicted at FIG. 4, may be adjusted based on calibration of one or more vehicle sensors. In still further examples, the vehicle may be equipped with an ultrasonic sensor that may be utilized for various automotive driver assistance systems (ADAS). Shown in FIG. 5 is an example ADAS comprising a parking assistance system, which may benefit from an accurately calibrated ultrasonic sensor.

Figure 6:
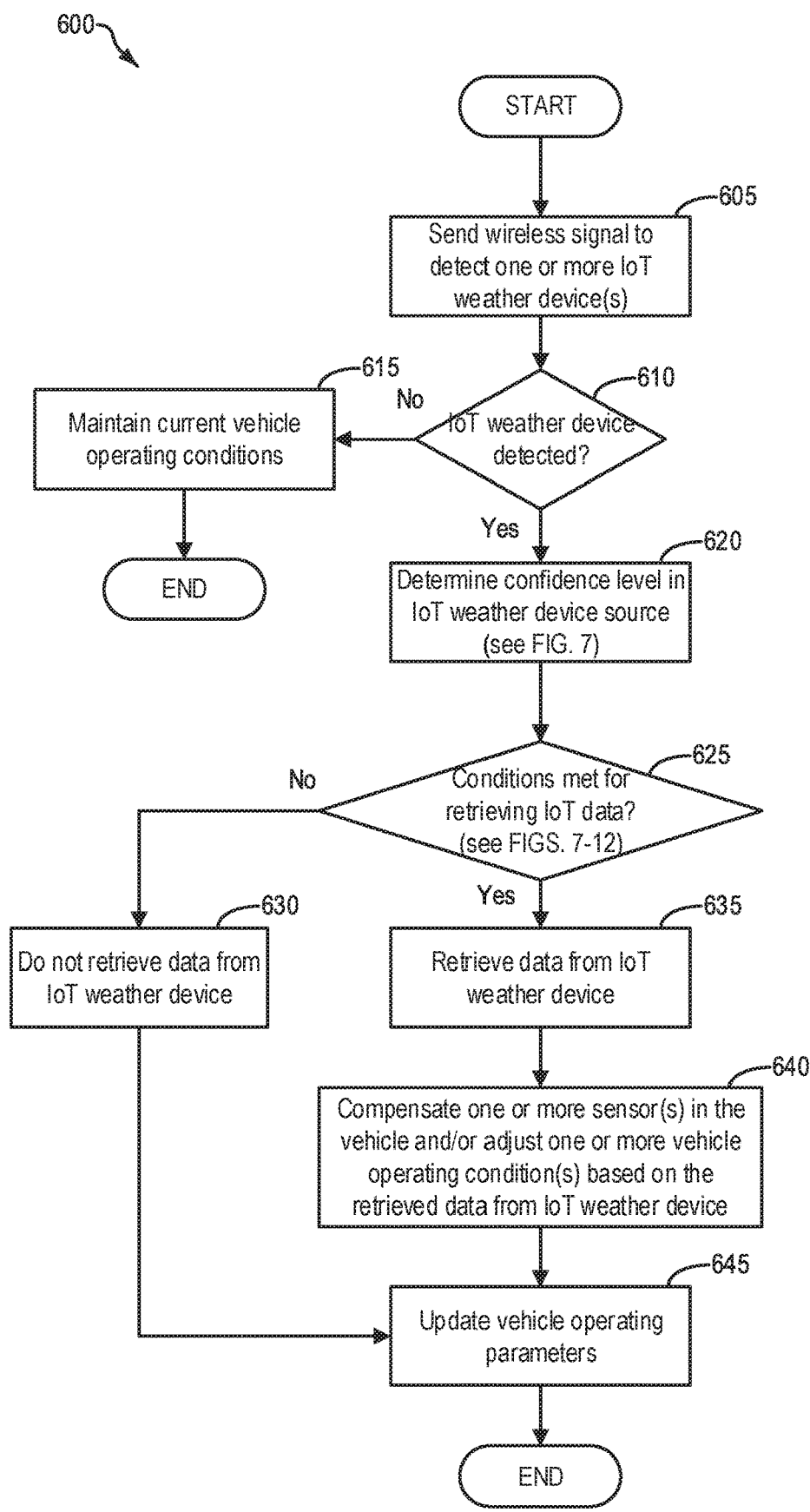
FIG. 6 depicts a high-level example method for retrieving data from one or more internet of things (IoT) weather devices, and using said data for adjusting and/or compensating one or more vehicle sensor(s) and/or vehicle operating parameter(s).

Accordingly, a high-level example method for calibrating various vehicular sensors is illustrated at FIG. 6. The method may include indicating a confidence level of a source of one or more IoT weather devices, and may further include calibrating the various vehicular sensors based on the confidence level and further based on whether conditions are indicated to be met for calibrating the various sensors. For example, a number of lookup tables stored at a controller of a vehicle may be utilized to determine whether conditions are indicated to be met for calibration of the various sensors, based on whether a source of the IoT weather devices comprises a high, medium, or low confidence level. Such lookup tables are illustrated at FIGS. 7-12.

Figure 13:
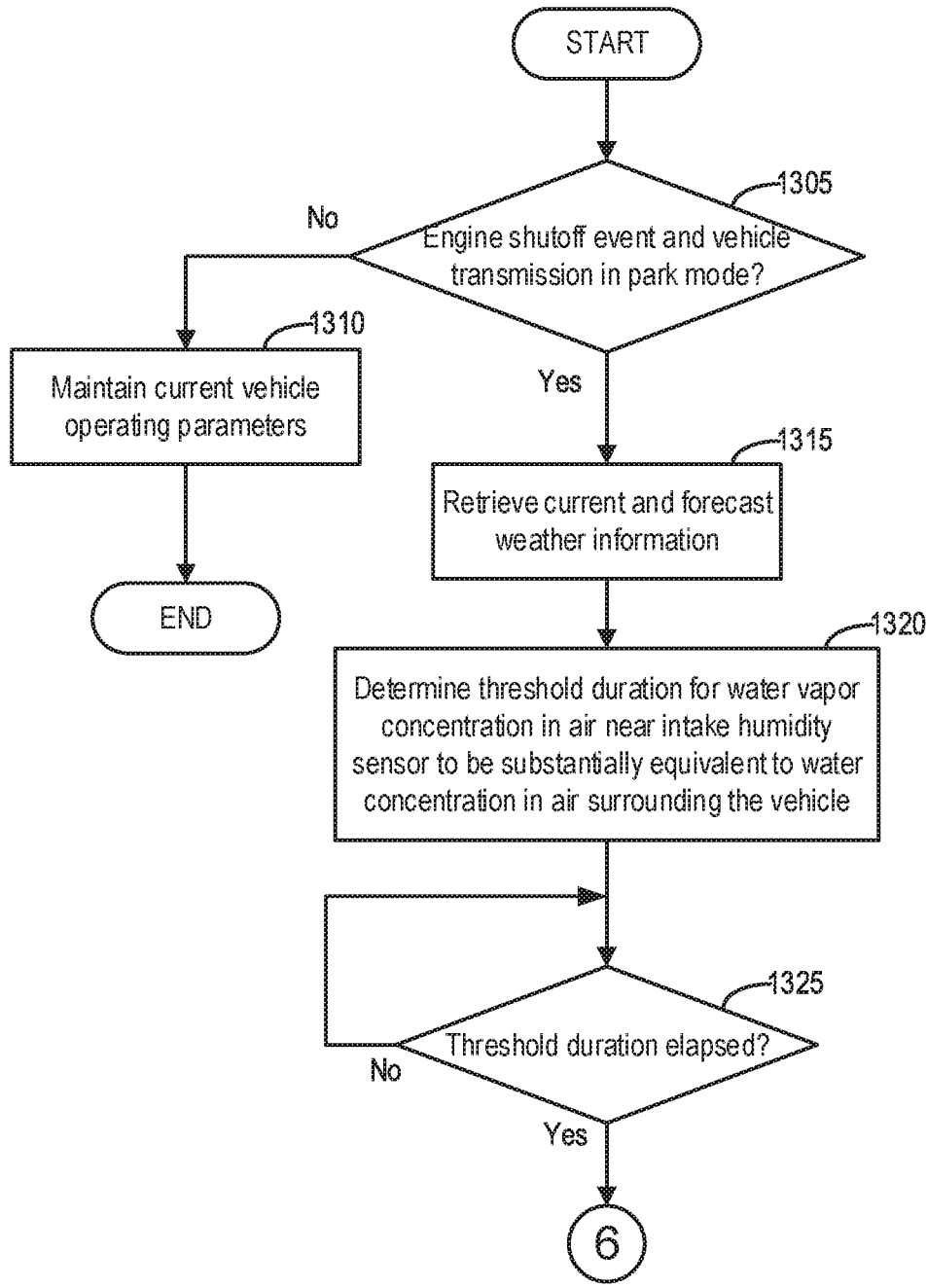
FIG. 13 depicts a high-level example method for calibrating a vehicle's engine intake humidity sensor.

In one example, conditions being met for calibration of an intake humidity sensor may comprise an indication that a concentration of water vapor in air near the intake humidity sensor is substantially equivalent to the concentration of water vapor in air external to (e.g. surrounding) the vehicle. Such a method for determining whether the concentration of water vapor in air near the intake humidity sensor is substantially equivalent to the concentration of water vapor in air external to the vehicle, is depicted at FIG. 13.

Figure 14:
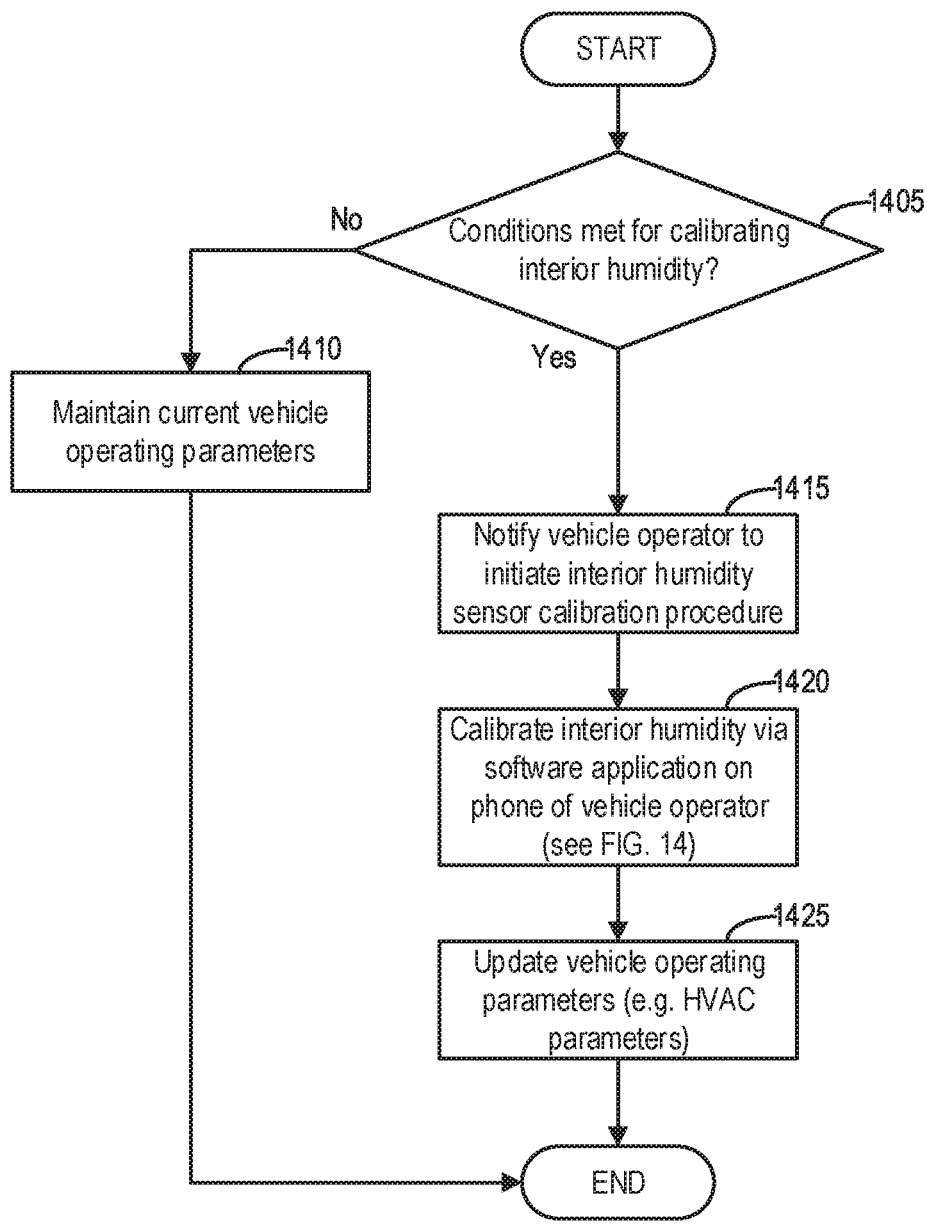
FIG. 14 depicts a high-level example method for calibrating a vehicle's interior humidity sensor.
Figure 15:
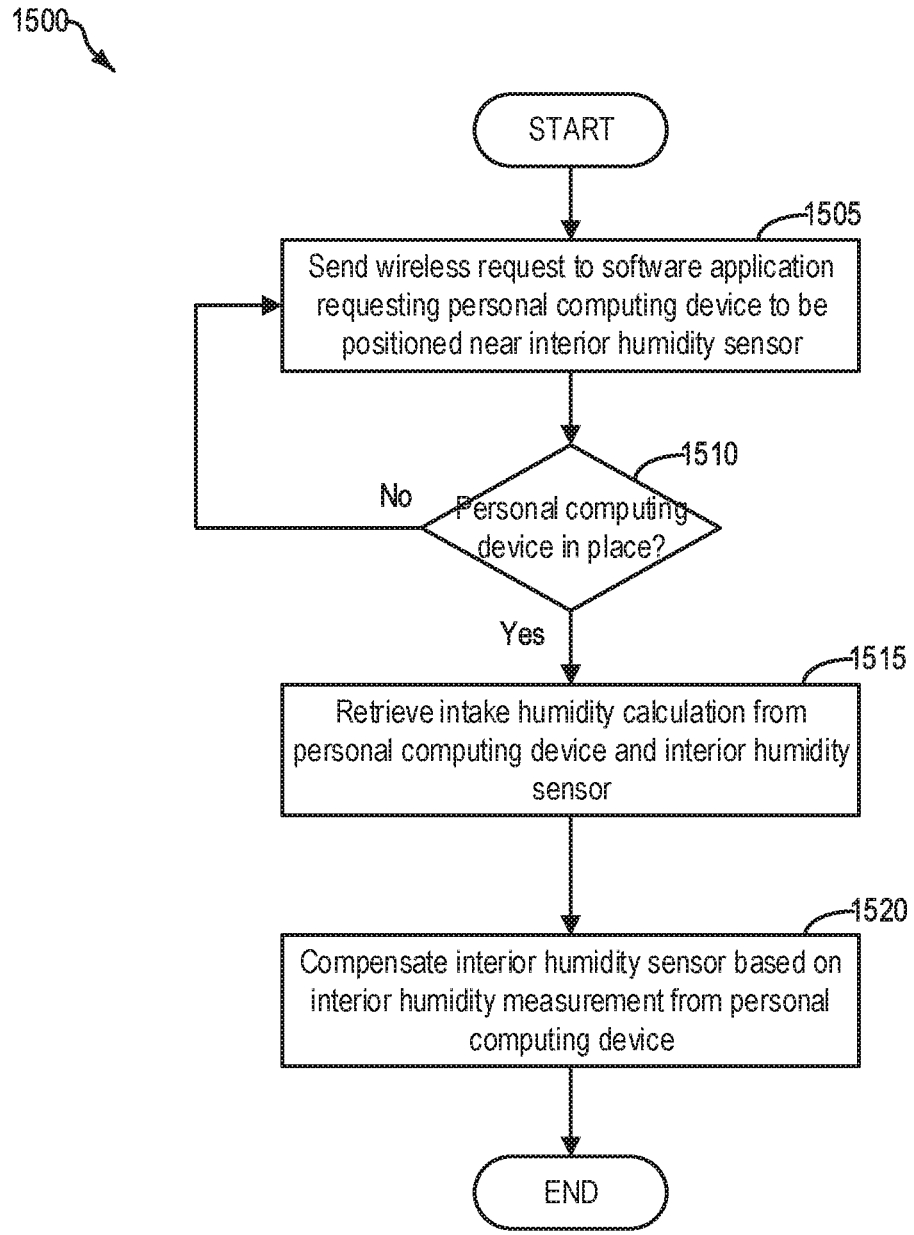
FIG. 15 depicts a high-level example method for utilizing a software application on a personal computing device to calibrate a vehicle's interior humidity sensor.

In another example, a method for calibrating an interior humidity sensor positioned inside a cabin of the vehicle is depicted at FIG. 14. In such an example, an IoT weather device positioned external to, and removed from, the vehicle may not be utilized to calibrate the interior humidity sensor, and instead, a personal computing device may be utilized to calibrate the interior humidity sensor. In such an example, a software application stored on the personal computing device may provide instructions to a vehicle operator or user of the personal computing device, as to how to calibrate the interior humidity sensor. Accordingly, FIG. 15 depicts a method whereby the software application may be utilized to calibrate the interior humidity sensor.

Figure 1:
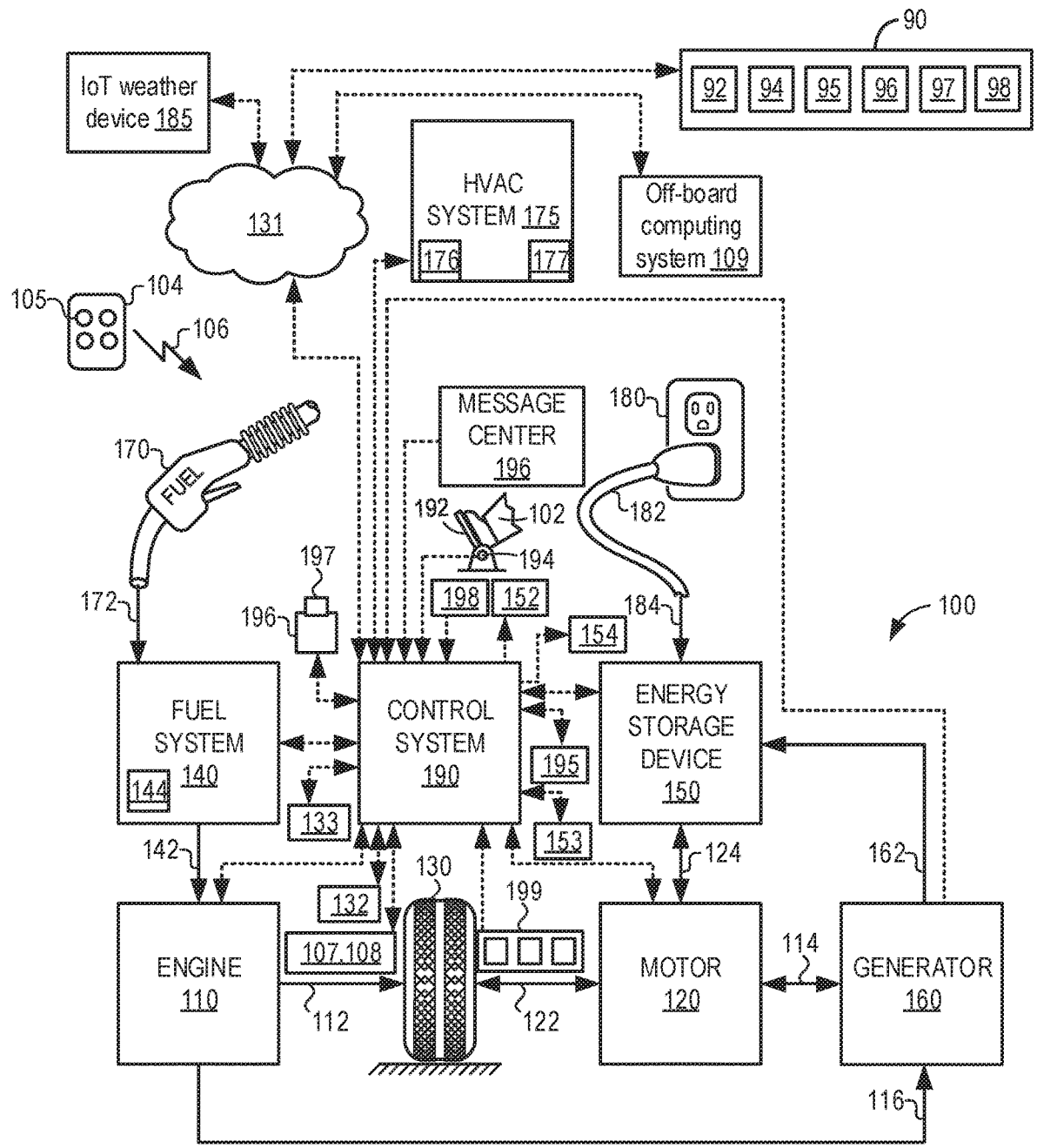
FIG. 1 schematically shows an example vehicle propulsion system.

Turning now to the figures, FIG. 1 illustrates an example vehicle propulsion system 100. Vehicle propulsion system 100 includes a fuel burning engine 110 and a motor 120. As a non-limiting example, engine 110 comprises an internal combustion engine and motor 120 comprises an electric motor. Motor 120 may be configured to utilize or consume a different energy source than engine 110. For example, engine 110 may consume a liquid fuel (e.g., gasoline) to produce an engine output while motor 120 may consume electrical energy to produce a motor output. As such, a vehicle with propulsion system 100 may be referred to as a hybrid electric vehicle (HEV). While vehicle propulsion system 100 is illustrated at FIG. 1 as a hybrid vehicle, it may be understood that in other examples, vehicle propulsion system 100 may not comprise a hybrid vehicle, without departing from the scope of this disclosure.

Vehicle propulsion system 100 may utilize a variety of different operational modes depending on operating conditions encountered by the vehicle propulsion system. Some of these modes may enable engine 110 to be maintained in an off state (i.e., set to a deactivated state) where combustion of fuel at the engine is discontinued. For example, under select operating conditions, motor 120 may propel the vehicle via drive wheel 130 as indicated by arrow 122 while engine 110 is deactivated.

During other operating conditions, engine 110 may be set to a deactivated state (as described above) while motor 120 may be operated to charge energy storage device 150. For example, motor 120 may receive wheel torque from drive wheel 130 as indicated by arrow 122 where the motor may convert the kinetic energy of the vehicle to electrical energy for storage at energy storage device 150 as indicated by arrow 124. This operation may be referred to as regenerative braking of the vehicle. Thus, motor 120 can provide a generator function in some examples. However, in other examples, generator 160 may instead receive wheel torque from drive wheel 130, where the generator may convert the kinetic energy of the vehicle to electrical energy for storage at energy storage device 150 as indicated by arrow 162.

During still other operating conditions, engine 110 may be operated by combusting fuel received from fuel system 140 as indicated by arrow 142. For example, engine 110 may be operated to propel the vehicle via drive wheel 130 as indicated by arrow 112 while motor 120 is deactivated. During other operating conditions, both engine 110 and motor 120 may each be operated to propel the vehicle via drive wheel 130 as indicated by arrows 112 and 122, respectively. A configuration where both the engine and the motor may selectively propel the vehicle may be referred to as a parallel type vehicle propulsion system. Note that in some examples, motor 120 may propel the vehicle via a first set of drive wheels and engine 110 may propel the vehicle via a second set of drive wheels.

In other examples, vehicle propulsion system 100 may be configured as a series type vehicle propulsion system, whereby the engine does not directly propel the drive wheels. Rather, engine 110 may be operated to power motor 120, which may in turn propel the vehicle via drive wheel 130 as indicated by arrow 122. For example, during select operating conditions, engine 110 may drive generator 160 as indicated by arrow 116, which may in turn supply electrical energy to one or more of motor 120 as indicated by arrow 114 or energy storage device 150 as indicated by arrow 162. As another example, engine 110 may be operated to drive motor 120 which may in turn provide a generator function to convert the engine output to electrical energy, where the electrical energy may be stored at energy storage device 150 for later use by the motor.

Fuel system 140 may include one or more fuel storage tanks 144 for storing fuel on-board the vehicle. For example, fuel tank 144 may store one or more liquid fuels, including but not limited to: gasoline, diesel, and alcohol fuels. In some examples, the fuel may be stored on-board the vehicle as a blend of two or more different fuels. For example, fuel tank 144 may be configured to store a blend of gasoline and ethanol (e.g., E10, E85, etc.) or a blend of gasoline and methanol (e.g., M10, M85, etc.), whereby these fuels or fuel blends may be delivered to engine 110 as indicated by arrow 142. Still other suitable fuels or fuel blends may be supplied to engine 110, where they may be combusted at the engine to produce an engine output. The engine output may be utilized to propel the vehicle as indicated by arrow 112 or to recharge energy storage device 150 via motor 120 or generator 160.

In some examples, energy storage device 150 may be configured to store electrical energy that may be supplied to other electrical loads residing on-board the vehicle (other than the motor), including cabin heating and air conditioning, engine starting, headlights, cabin audio and video systems, etc. As a non-limiting example, energy storage device 150 may include one or more batteries and/or capacitors.

Control system 190 may communicate with one or more of engine 110, motor 120, fuel system 140, energy storage device 150, and generator 160. Control system 190 may receive sensory feedback information from one or more of engine 110, motor 120, fuel system 140, energy storage device 150, and generator 160. Further, control system 190 may send control signals to one or more of engine 110, motor 120, fuel system 140, energy storage device 150, and generator 160 responsive to this sensory feedback. Control system 190 may receive an indication of an operator requested output of the vehicle propulsion system from a vehicle operator 102. For example, control system 190 may receive sensory feedback from pedal position sensor 194 which communicates with pedal 192. Pedal 192 may refer schematically to a brake pedal and/or an accelerator pedal. Furthermore, in some examples control system 190 may be in communication with a remote engine start receiver 195 (or transceiver) that receives wireless signals 106 from a key fob 104 having a remote start button 105. In other examples (not shown), a remote engine start may be initiated via a cellular telephone, or smartphone based system where a user's cellular telephone sends data to a server and the server communicates with the vehicle to start the engine.

The control system 190 may be communicatively coupled to an off-board remote computing device 90 and an off-board computing system 109 via a wireless network 131, which may comprise Wi-Fi, Bluetooth, a type of cellular service, a wireless data transfer protocol, and so on. The remote computing device 90 may comprise, for example, a processor 92 for executing instructions, a memory 94 for storing said instructions, a user interface 95 for enabling user input (e.g., a keyboard, a touch screen, a mouse, a microphone, a camera, etc.), and a display 96 for displaying graphical information. As such, the remote computing device 90 may comprise any suitable computing device, such as a personal computer (e.g., a laptop, a tablet, etc.), a smart device (e.g., a smart phone, etc.), and so on. As described further herein and with regard to FIGS. 14-15, the control system 190 may be configured to transmit information regarding status of vehicle interior humidity to remote computing device 90, which may in turn display the information via display 96. More specifically, the vehicle control system may in some examples alert a vehicle operator via the remote computing device 90 of a request to conduct a calibration or compensation procedure for interior humidity sensor 152. In other examples, such a request may be communicated to the vehicle operator via the vehicle instrument panel 196. As will be described in further detail in FIGS. 14-15, in response to a request to calibrate the vehicle's interior humidity sensor 152, the vehicle operator may utilize an application (software app) on computing device 90 which may instruct the vehicle operator as to how to conduct the interior humidity sensor calibration. Briefly, personal computing device 90 may include a humidity sensor 97, which may be utilized to compensate the vehicle's interior humidity sensor (e.g. 152). In some examples, personal computing device 90 may additionally include a camera 98, which may include capabilities such as video, for example. In one example, the camera 98 may be utilized in conjunction with the software application on the computing device 90 to enable the vehicle operator to conduct the interior humidity sensor calibration. For example, the camera may be utilized to indicate when placement of the computing device 90 is within a predetermined threshold of the vehicle's interior humidity sensor. In one example, the camera may include object recognition software that may be utilized to position the camera within the predetermined threshold of the vehicle's interior humidity sensor. It may be understood that any method known by those skilled in the art may be utilized to conduct object recognition via the use of one or more camera(s). As an illustrative example, one method of object recognition may include edge detection techniques, such as the Canny edge detection, to find edges in an image frame acquired by the one or more cameras. An edge-image corresponding to the image frame may then be generated. Furthermore, a binary image corresponding to the edge-image may also be generated. Subsequently, one or more "blobs" in the binary image corresponding to one or more objects, or obstacles, may be identified. Based on an analysis of the blobs in the binary image, information such as shape, relative size, relative distance, etc., of each of the blobs corresponding to objects may be determined. As discussed, such an example is meant to be illustrative, and is not meant to be limiting. Other methods and systems for object detection via the use of one or more cameras that are known in the art may be readily utilized without departing from the scope of the present disclosure.

Off-board computing system 109 may include a computing system capable of communicating weather information or other information to the controller. For example, the off-board computing system 109 may be configured to communicate current and forecast weather information to the vehicle controller. In some examples, information from the off-board computing system 109 may be cross-referenced to the internet, for example.

Energy storage device 150 may periodically receive electrical energy from a power source 180 residing external to the vehicle (e.g., not part of the vehicle) as indicated by arrow 184. As a non-limiting example, vehicle propulsion system 100 may be configured as a plug-in hybrid electric vehicle (HEV), whereby electrical energy may be supplied to energy storage device 150 from power source 180 via an electrical energy transmission cable 182. During a recharging operation of energy storage device 150 from power source 180, electrical transmission cable 182 may electrically couple energy storage device 150 and power source 180. While the vehicle propulsion system is operated to propel the vehicle, electrical transmission cable 182 may disconnected between power source 180 and energy storage device 150. Control system 190 may identify and/or control the amount of electrical energy stored at the energy storage device, which may be referred to as the state of charge (SOC).

In other examples, electrical transmission cable 182 may be omitted, where electrical energy may be received wirelessly at energy storage device 150 from power source 180. For example, energy storage device 150 may receive electrical energy from power source 180 via one or more of electromagnetic induction, radio waves, and electromagnetic resonance. As such, it should be appreciated that any suitable approach may be used for recharging energy storage device 150 from a power source that does not comprise part of the vehicle. In this way, motor 120 may propel the vehicle by utilizing an energy source other than the fuel utilized by engine 110.

Fuel system 140 may periodically receive fuel from a fuel source residing external to the vehicle. As a non-limiting example, vehicle propulsion system 100 may be refueled by receiving fuel via a fuel dispensing device 170 as indicated by arrow 172. In some examples, fuel tank 144 may be configured to store the fuel received from fuel dispensing device 170 until it is supplied to engine 110 for combustion. In some examples, control system 190 may receive an indication of the level of fuel stored at fuel tank 144 via a fuel level sensor. The level of fuel stored at fuel tank 144 (e.g., as identified by the fuel level sensor) may be communicated to the vehicle operator, for example, via a fuel gauge or indication in a vehicle instrument panel 196.

The vehicle propulsion system 100 may also include an external (e.g. external to the interior cabin of the vehicle) humidity sensor 198, an interior (e.g. inside the vehicle cabin) humidity sensor 152, a dedicated barometric pressure (BP) sensor 153, an outside air temperature sensor 154, and a roll stability control sensor, such as a lateral and/or longitudinal and/or yaw rate sensor(s) 199. While vehicle propulsion system 100 is indicated to include external humidity sensor 198, it may be understood that in some examples, vehicle propulsion system 100 may not include external humidity sensor 198. Similarly, while vehicle propulsion system 100 is indicated to include dedicated BP sensor 153, in some examples, vehicle propulsion system 100 may not include dedicated BP sensor 153. Furthermore, it may be understood that dedicated BP sensor 153 may be positioned external to engine 110, and may be configured for measuring outdoor BP. The vehicle instrument panel 196 may include indicator light(s) and/or a text-based display in which messages are displayed to an operator. The vehicle instrument panel 196 may also include various input portions for receiving an operator input, such as buttons, touch screens, voice input/recognition, etc. For example, the vehicle instrument panel 196 may include a refueling button 197 which may be manually actuated or pressed by a vehicle operator to initiate refueling. For example, as described in more detail below, in response to the vehicle operator actuating refueling button 197, a fuel tank in the vehicle may be depressurized so that refueling may be performed.

Vehicle propulsion system 100 may also include a heating, ventilation, and air conditioning system (HVAC) 175. HVAC system may include an air conditioning system 176, and a vehicle cooling system 177, as will be discussed in further detail below.

Control system 190 may be communicatively coupled to other vehicles or infrastructures using appropriate communications technology, as is known in the art. For example, control system 190 may be coupled to other vehicles or infrastructures via a wireless network 131, which may comprise Wi-Fi, Zigbee, Z-wave, Bluetooth, a type of cellular service, a wireless data transfer protocol, and so on. Control system 190 may broadcast (and receive) information regarding vehicle data, vehicle diagnostics, traffic conditions, vehicle location information, vehicle operating procedures, etc., via vehicle-to-vehicle (V2V), vehicle-to-infrastructure-to-vehicle (V2I2V), and/or vehicle-to-infrastructure (V2I) technology. The communication and the information exchanged between vehicles can be either direct between vehicles, or can be multi-hop. In some examples, longer range communications (e.g. WiMax) may be used in place of, or in conjunction with, V2V, or V2I2V, to extend the coverage area by a few miles. In still other examples, vehicle control system 190 may be communicatively coupled to other vehicles or infrastructures via a wireless network 131 and the internet (e.g. cloud), as is commonly known in the art. In some examples, control system may be coupled to other vehicles or infrastructures (e.g. off-board computing system 109) via wireless network 131.

In some examples, control system 190 may be communicatively coupled to one or more "internet of things" (IoT) weather device(s) 185, via wireless network 131 (which may include Wi-Fi, Zigbee, Z-wave, Bluetooth, a type of cellular service, a wireless data transfer protocol, etc.). For example, IoT weather devices 185 may comprise devices equipped with one or more sensor(s), for measuring one or more parameters, such as barometric pressure, humidity, temperature, wind speed and direction, etc. Discussed herein, it may be understood that IoT weather devices may comprise weather devices with network connectivity that enables said devices to collect and exchange weather data. For example, a plurality of IoT weather devices may in some examples exchange data related to various weather-related parameters with/between one another. In another example, one or more IoT weather devices may additionally or alternatively exchange data with vehicle control system 190, as discussed above.

Vehicle system 100 may also include an on-board navigation system 132 (for example, a Global Positioning System) that an operator of the vehicle may interact with. The navigation system 132 may include one or more location sensors for assisting in estimating vehicle speed, vehicle altitude, vehicle position/location, etc. This information may be used to infer engine operating parameters, such as local barometric pressure. As discussed above, control system 190 may further be configured to receive information via the internet or other communication networks. Information received from the GPS may be cross-referenced to information available via the internet to determine local weather conditions, local vehicle regulations, etc. In some examples, other sensors, such as lasers, radar, sonar, acoustic sensors, etc, (e.g. 133) may additionally be included in vehicle propulsion system 100.

In some examples, vehicle control system 190 may be further communicatively coupled to one or more rain sensors 107. Such sensors may be configured to report to the vehicle control system the presence of rain, snow, etc. In other examples, the vehicle control system may be communicatively coupled to one or more onboard cameras 108 configured to monitor immediate surroundings of the vehicle. In some examples, the one or more onboard cameras 108 may enable an accurate determination of whether it is raining, snowing, etc., outside, and whether the vehicle is experiencing the rain/snow, etc.

FIG. 2 shows another example embodiment of vehicle propulsion system 100. FIG. 2 shows an example embodiment of vehicle 202 with an air conditioning system 176 coupled to engine 110. Further, vehicle 202 may include final drive/wheels 206, which may contact a road surface.

Air conditioning system 176 includes a compressor 230, a condenser 232, and an evaporator 236 for providing cooled air to the vehicle passenger compartment 204. Compressor 230 receives refrigerant gas from evaporator 236 and pressurizes the refrigerant. Compressor 230 may include a clutch 210, which may be selectively engaged and disengaged, or partially engaged, to supply compressor 230 with rotational energy from engine 110, via a drive pulley/belt 211. In this way, compressor 230 is mechanically driven by engine 110 through clutch 210 via belt 211. The controller may adjust a load of compressor 230 by actuating clutch 210 through a clutch relay or other electric switching device. In one example, the controller may increase the load of compressor 230 in response to a request for air conditioning. In another example, compressor 230 may be a variable displacement AC compressor and may include a variable displacement control valve. After compressor 230 receives and pressurizes the refrigerant gas, heat is extracted from the pressurized refrigerant so that the refrigerant is liquefied at condenser 232. A drier 233 may be coupled to condenser 232 to reduce undesired moisture (e.g. water) from the air conditioning system 240. In some embodiments, drier 233 may include a filter (not shown) to remove particulates. After being pumped into condenser 232, refrigerant is supplied to evaporator 236 via evaporator valve 234. The liquefied refrigerant expands after passing through evaporator valve 234 causing a reduction in temperature. In this way, air temperature in passenger compartment 204 may be reduced by flowing air across evaporator 236 via fan 237.

More specifically, cooled air from evaporator 236 may be directed to passenger compartment 204 through ventilation duct 245, illustrated by arrows 291. Controller 12 operates fan 237 according to operator settings, which may be inputted using vehicle instrument panel 298, as well as climate sensors. Within the passenger compartment (e.g. cabin), a vehicle operator or passenger may input desired air conditioning parameters via a vehicle instrument panel 196. In one example, the vehicle instrument panel 196 may comprise one or more of input portions for receiving an operator input, such as buttons, touch screens, voice input/recognition, etc. In the depicted example, vehicle instrument panel 196 may include input portions for receiving operator input for the air conditioning system 176 (e.g. on/off state of the air conditioning system, desired passenger compartment temperature, fan speed, and distribution path for conditioned cabin air). Further, the vehicle instrument panel 196 may include one or more of indicator lights and/or a text-based display with which messages are displayed to an operator. In another example, a plurality of sensors 30 may include one or more climate sensors, which may indicate the temperature of evaporator 236 and passenger compartment 204, as well as ambient temperature, to controller 12. Further, sensors 30 may include humidity sensors (e.g. 152) to measure the humidity of passenger compartment 204.

FIG. 2 further shows control system 190. Control system 190 is the control system 190 shown in FIG. 1, including controller 12, which may receive input from a plurality of sensors 30 and may communicate with various actuators 32. The controller 12 receives signals from the various sensors of FIG. 2 and employs the various actuators of FIG. 2 to adjust engine operation and air conditioner operation based on the received signals and instructions stored on a memory of the controller.

FIG. 3 shows an example embodiment of vehicle propulsion system 100 including a vehicle cooling system 177 in vehicle 202. Vehicle 202 has drive wheels 206, passenger compartment 204 (herein also referred to as a passenger cabin), and an under-hood compartment 303. Under-hood compartment 303 may house various under-hood components under the hood (not shown) of motor vehicle 202. For example, under-hood compartment 303 may house internal combustion engine 110. Internal combustion engine 110 has one or more combustion chambers which may receive intake air via intake passage 344 and may exhaust combustion gases via exhaust passage 348.

Under-hood compartment 303 may further include cooling system 177 that circulates coolant through internal combustion engine 110 to absorb waste heat, and distributes the heated coolant to radiator 380 and/or heater core 390 via coolant lines (or loops) 382 and 384, respectively. In one example, as depicted, cooling system 177 may be coupled to engine 110 and may circulate engine coolant from engine 110 to radiator 380 via engine-driven water pump 386, and back to engine 110 via coolant line 382. Engine-driven water pump 386 may be coupled to the engine via front end accessory drive (FEAD) 360, and rotated proportionally to engine speed via a belt, chain, etc. Specifically, engine-driven pump 386 may circulate coolant through passages in the engine block, head, etc., to absorb engine heat, which is then transferred via the radiator 380 to ambient air. In one example, where pump 386 is a centrifugal pump, the pressure (and resulting flow) produced by the pump may be increased with increasing crankshaft speed, which may be directly linked to the engine speed. In some examples, engine-driven pump 386 may operate to circulate the coolant through both coolant lines 382 and 384.

The temperature of the coolant may be regulated by a thermostat 338. Thermostat 338 may include a temperature sensing element 315, located at the junction of cooling lines 382, 385, and 384. Further, thermostat 338 may include a thermostat valve 341 located in cooling line 382. In some examples, the thermostat valve may remain closed until the coolant reaches a threshold temperature, thereby limiting coolant flow through the radiator until the threshold temperature is reached.

Coolant may flow through coolant line 384 to heater core 390 where the heat may be transferred to passenger compartment 204. Then, coolant flows back to engine 110 through valve 322. Specifically, heater core 390, which is configured as a water-to-air heat exchanger, may exchange heat with the circulating coolant and transfer the heat to the vehicle passenger compartment 204 based in operator heating demands. For example, based on a cabin heating/cooling request received from the operator, the cabin air may be warmed using the heated coolant at the heater core 390 to raise cabin temperatures and provide cabin heating. In general, the heat priority may include cabin heating demands being met first, followed by combustion chamber heating demands being met, followed by powertrain fluid/lubricant heating demands being met. However, various conditions may alter this general priority. Ideally, no heating would be rejected by the radiator until all the above components are at full operating temperature. As such, heat exchanger limits reduce the efficiency of the system.

Coolant may also circulate from engine 110 towards thermostat 338 upon passage through a first bypass loop 385 via a first bypass shut-off valve 321. During selected conditions, such as during an engine cold-start condition, bypass shut-off valve 321 may be closed to stagnate a (small) amount of coolant in bypass loop 385, at the engine block and cylinder heads. By isolating coolant at the engine block, coolant flow past the thermostat's temperature sensing element 315 may be prevented, thus delaying opening of the thermostatic valve 341 allowing flow to the radiator. In other words, coolant circulation is enabled in first bypass loop 385 when thermostat valve 341 is closed, bypass shut-off valve 321 is closed, and the coolant pump speed is high. This coolant circulation limits the coolant pressure and pump cavitation. Overall, engine warm-up may be expedited by reducing flow to thermal losses outside the engine and by preventing the temperature sensing element 315 from seeing hot coolant flow from the engine. Coolant may be circulated from heater core 390 towards thermostat 338 via heater shut-off valve 322. During engine cold-start conditions, heater shut-off valve may also be closed to stagnate a small amount of coolant in cooling line (or loop) 384. This also allows coolant to be stagnated at the engine block, heater core, and cylinder heads, further assisting in engine and transmission warm-up.

It will be appreciated that while the above example shows stagnating coolant at the engine by adjusting a position of one or more valves, in alternate embodiments, such as when using an electrically-driven coolant/heatant pump, coolant stagnation at the engine may also be achieved by controlling the pump speed to zero.

One or more blowers and cooling fans may be included in cooling system 177 to provide airflow assistance and augment a cooling airflow through the under-hood components. For example, cooling fan 392, coupled to radiator 380, may be operated to provide cooling airflow assistance through radiator 380. Cooling fan 392 may draw a cooling airflow into under-hood compartment 303 through an opening in the front-end of vehicle 202, for example, through grill shutter system 312. Such a cooling air flow may then be utilized by radiator 380 and other under-hood components (e.g., fuel system components, batteries, etc.) to keep the engine and/or transmission cool. Further, the air flow may be used to reject heat from a vehicle air conditioning system. Further still, the airflow may be used to improve the performance of a turbocharged/supercharged engine that is equipped with intercoolers that reduce the temperature of the air that goes into the intake manifold/engine. In one example, grill shutter system 312 may be configured with a plurality of louvers (or fins, blades, or shutters) wherein a controller may adjust a position of the louvers to control an airflow through the grill shutter system.

Cooling fan 392 may be coupled to, and driven by, engine 110, via alternator 372 and system battery 374. In some examples, system battery 374 may be the same as energy storage device 150 depicted at FIG. 1. Cooling fan 392 may also be mechanically coupled to engine 110 via an optional clutch (not shown). During engine operation, the engine generated torque may be transmitted to alternator 372 along a drive shaft (not shown). The generated torque may be used by alternator 372 to generate electrical power, which may be stored in an electrical energy storage device, such as system battery 374. Battery 374 may then be used to operate an electric cooling fan motor 394.

Vehicle system 100 may further include a transmission 340 for transmitting the power generated at engine 110 to vehicle wheels 106. Transmission 340, including various gears and clutches, may be configured to reduce the high rotational speed of the engine to a lower rotational speed of the wheel, while increasing torque in the process. To enable temperature regulation of the various transmission components, cooling system 177 may also be communicatively coupled to a transmission cooling system 345. The transmission cooling system 345 includes a transmission oil cooler 325 (or oil-to-water transmission heat exchanger) located internal or integral to the transmission 340, for example, in the transmission sump area at a location below and/or offset from the transmission rotating elements. Transmission oil cooler 325 may have a plurality of plate or fin members for maximum heat transfer purposes. Coolant from coolant line 384 may communicate with transmission oil cooler 325 via conduit 346 and transmission warming valve 323. Specifically, transmission warming valve 323 may be opened to receive heated coolant from coolant line 384 to warm transmission 340. In comparison, coolant from coolant line 382 and radiator 380 may communicate with transmission oil cooler 325 via conduit 348 and transmission cooling valve 324. Specifically, transmission cooling valve 324 may be opened to receive cooled coolant from radiator 380 for cooling transmission 340.

FIG. 3 further shows a control system 190. Control system 190 may be communicatively coupled to various components of engine 110 to carry out the control routines and actions described herein. For example, as discussed above, control system 190 may include an electronic digital controller 12. Controller 12 may be a microcomputer, including a microprocessor unit, input/output ports, an electronic storage medium for executable programs and calibration values, random access memory, keep alive memory, and a data bus. As depicted, controller 12 may receive input from a plurality of sensors 30, which may include user inputs and/or sensors (such as transmission gear position, gas pedal input, brake input, transmission selector position, vehicle speed, engine speed, mass airflow through the engine, ambient temperature, intake air temperature, etc.), cooling system sensors (such as coolant temperature, cylinder heat temperature, fan speed, passenger compartment temperature, ambient humidity, thermostat output, etc.), and others. Further, controller 12 may communicate with various actuators 32, which may include engine actuators (such as fuel injectors, an electronically controlled intake air throttle plate, spark plugs, etc.), cooling system actuators (such as the various valves of the cooling system), and others. In some examples, the storage medium may be programmed with computer readable data representing instructions executable by the processor for performing the methods described below as well as other variants that are anticipated but not specifically listed.

Figure 4:
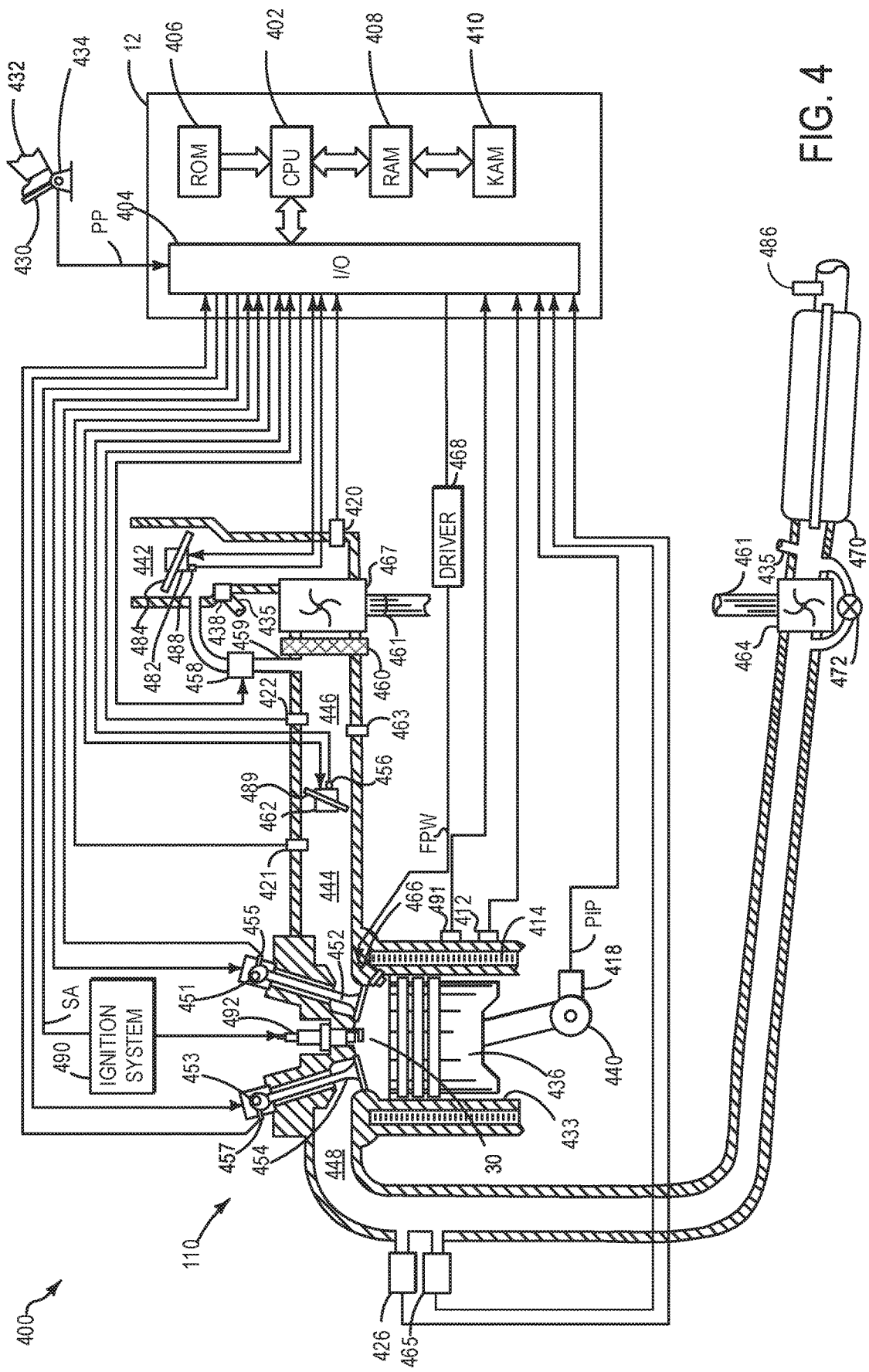
FIG. 4 is a schematic diagram of an engine.
Figure 5:
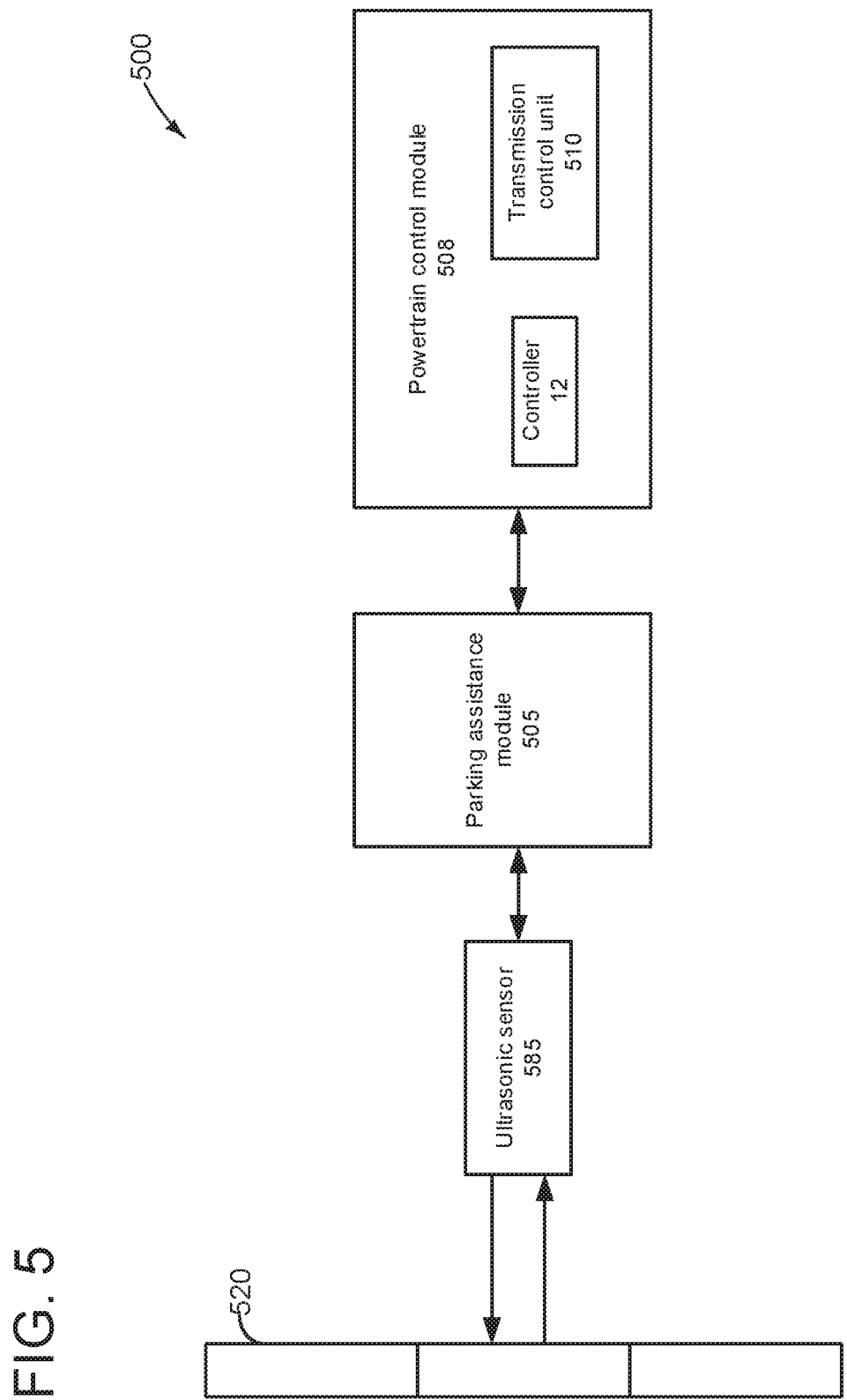
FIG. 5 shows a block diagram of components of a vehicle system that uses ultrasonic sensor(s) for assisting or controlling vehicle parking maneuvers.

FIG. 4 depicts an engine system 400 for a vehicle. The vehicle may be an on-road vehicle (e.g. 202) having drive wheels which contact a road surface. Engine system 400 includes engine 110 which comprises a plurality of cylinders. FIG. 1 describes one such cylinder or combustion chamber in detail. The various components of engine 110 may be controlled by electronic engine controller 12. Engine 110 includes combustion chamber 201 and cylinder walls 433 with piston 436 positioned therein and connected to crankshaft 440. Combustion chamber 201 is shown communicating with intake manifold 444 and exhaust manifold 448 via respective intake valve 452 and exhaust valve 454. Each intake and exhaust valve may be operated by an intake cam 451 and an exhaust cam 453. Alternatively, one or more of the intake and exhaust valves may be operated by an electromechanically controlled valve coil and armature assembly. The position of intake cam 451 may be determined by intake cam sensor 455. The position of exhaust cam 453 may be determined by exhaust cam sensor 457.

Fuel injector 466 is shown positioned to inject fuel directly into cylinder 201, which is known to those skilled in the art as direct injection. Alternatively, fuel may be injected to an intake port, which is known to those skilled in the art as port injection. Fuel injector 466 delivers liquid fuel in proportion to the pulse width of signal FPW from controller 12. Fuel is delivered to fuel injector 466 by a fuel system (not shown) including a fuel tank, fuel pump, and fuel rail. Fuel injector 466 is supplied operating current from driver 468 which responds to controller 12. In addition, intake manifold 444 is shown communicating with optional electronic throttle 462 which adjusts a position of throttle plate 489 to control airflow to engine cylinder 201. This may include controlling airflow of boosted air from intake boost chamber 446. In some embodiments, throttle 462 may be omitted and airflow to the engine may be controlled via a single air intake system throttle (AIS throttle) 482 coupled to air intake passage 442 and located upstream of the boost chamber 446.

In some embodiments, engine 110 is configured to provide exhaust gas recirculation, or EGR. When included, EGR is provided via EGR passage 435 and EGR valve 438 to the engine air intake system at a position downstream of air intake system (AIS) throttle 482 from a location in the exhaust system downstream of turbine 464. EGR may be drawn from the exhaust system to the intake air system when there is a pressure differential to drive the flow. A pressure differential can be created by partially closing AIS throttle 482. Throttle plate 484 controls pressure at the inlet to compressor 467. The AIS may be electrically controlled and its position may be adjusted based on optional position sensor 488.

Compressor 467 draws air from air intake passage 442 to supply boost chamber 446. In some examples, air intake passage 442 may include an air box (not shown) with a filter. Exhaust gases spin turbine 464 which is coupled to compressor 467 via shaft 461. A vacuum operated wastegate actuator 472 allows exhaust gases to bypass turbine 464 so that boost pressure can be controlled under varying operating conditions. In alternate embodiments, the wastegate actuator may be pressure or electrically actuated. Wastegate 472 may be closed (or an opening of the wastegate may be decreased) in response to increased boost demand, such as during an operator pedal tip-in. By closing the wastegate, exhaust pressures upstream of the turbine can be increased, raising turbine speed and peak power output. This allows boost pressure to be raised. Additionally, the wastegate can be moved toward the closed position to maintain desired boost pressure when the compressor recirculation valve is partially open. In another example, wastegate 472 may be opened (or an opening of the wastegate may be increased) in response to decreased boost demand, such as during an operator pedal tip-out. By opening the wastegate, exhaust pressures can be reduced, reducing turbine speed and turbine power. This allows boost pressure to be lowered.

Compressor recirculation valve 458 (CRV) may be provided in a compressor recirculation path 459 around compressor 467 so that air may move from the compressor outlet to the compressor inlet so as to reduce a pressure that may develop across compressor 467. A charge air cooler 460 may be positioned in passage 446, downstream of compressor 467, for cooling the boosted aircharge delivered to the engine intake. In the depicted example, compressor recirculation path 459 is configured to recirculate cooled compressed air from downstream of charge air cooler 460 to the compressor inlet. In alternate examples, compressor recirculation path 459 may be configured to recirculate compressed air from downstream of the compressor and upstream of charge air cooler 460 to the compressor inlet. CRV 458 may be opened and closed via an electric signal from controller 12. CRV 458 may be configured as a three-state valve having a default semi-open position from which it can be moved to a fully-open position or a fully-closed position.

Distributorless ignition system 490 provides an ignition spark to combustion chamber 201 via spark plug 492 in response to controller 12. The ignition system 490 may include an induction coil ignition system, in which an ignition coil transformer is connected to each spark plug of the engine.

A first exhaust oxygen sensor 426 is shown coupled to exhaust manifold 448 upstream of catalytic converter 470. A second exhaust oxygen sensor 486 is shown coupled in the exhaust downstream of the converter 470. The first exhaust oxygen sensor 426 and the second exhaust oxygen sensor 486 may be any one of a Universal Exhaust Gas Oxygen (UEGO) sensor, a heated exhaust oxygen sensor (HEGO), or two-state exhaust oxygen sensor (EGO). The UEGO may be a linear sensor wherein the output is a linear pumping current proportional to an air-fuel ratio.

Additionally, an exhaust temperature sensor 465 is shown coupled to exhaust manifold 448 upstream of turbine 464. Output from the exhaust temperature sensor 465 may be used to learn an actual exhaust temperature. In addition, engine controller 12 may be configured to model a predicted exhaust temperature. For example, at a given engine speed and load, a flange temperature may be estimated. The results may then be used to populate a table of base temperatures. These temperatures may then be modified as a function of spark retard from MBT spark timing, air-fuel ratio, and EGR rate. The model may compensate for controlled late combustion, for example when it is controlled via known changes to a spark discharge location and timing, as commanded by the engine controller.

Converter 470 includes an exhaust catalyst. For example, the converter 470 can include multiple catalyst bricks. In another example, multiple emission control devices, each with multiple bricks, can be used. Converter 470 can be a three-way type catalyst in one example. While the depicted example shows first exhaust oxygen sensor 426 upstream of turbine 464, it will be appreciated that in alternate embodiments, the first exhaust oxygen sensor 426 may be positioned in the exhaust manifold downstream of turbine 464 and upstream of convertor 470. Further, the first exhaust oxygen sensor 426 may be referred to herein as the pre-catalyst oxygen sensor and the second exhaust oxygen sensor 486 may be referred to herein as the post-catalyst oxygen sensor.

The first and second oxygen sensors may give an indication of exhaust air-fuel ratio. For example, the second exhaust oxygen sensor 486 may be used for catalyst monitoring while the first exhaust oxygen sensor 426 may be used for engine control. Further, both the first exhaust oxygen sensor 426 and the second exhaust oxygen sensor 486 may operate at a switching frequency or response time in which the sensor switches between lean and rich air-fuel control (e.g., switches from lean to rich or from rich to lean). In one example, an exhaust oxygen sensor degradation rate may be based on the switching frequency of the sensor, the degradation rate increasing for decreasing switching frequency. In another example, the exhaust oxygen sensor degradation rate may be based on a response time of the exhaust oxygen sensor, the degradation rate increasing for decreasing response time. For example, if the sensor is a linear sensor (such as a UEGO), the sensor degradation rate may be based on the response time of the sensor. Alternatively, if the sensor is not a linear sensor (such as a HEGO), the sensor degradation rate may be based on the switching frequency of the sensor.

Engine 110 may further include one (as depicted) or more knock sensors 491 distributed along a body of the engine (e.g., along an engine block). When included, the plurality of knock sensors may be distributed symmetrically or asymmetrically along the engine block. Knock sensor 491 may be an accelerometer (e.g., vibration sensor), an ionization sensor, or an in-cylinder transducer. In one example, the controller 12 may be configured to detect and differentiate engine block vibrations generated due to abnormal combustion events, such as knocking and pre-ignition with the knock sensor 491. For example, abnormal combustion of higher than threshold intensity detected in an earlier crank angle window, before a spark event, may be identified as pre-ignition while abnormal combustion of higher than threshold intensity detected in a later crank angle window, after a spark event, may be identified as knock. In addition, the intensity thresholds may be different, the threshold for pre-ignition being higher than the threshold for knock. Mitigating actions responsive to knock and pre-ignition may also differ, with knock being addressed with spark retard while pre-ignition is addressed with cylinder enrichment or enleanment.

Further, the controller 12 may be configured to perform adaptive knock control. Specifically, the controller 12 may apply a certain amount of spark angle retard to the ignition timing in response to sensing knock with the knock sensor 491. The amount of spark retard at the current speed-load operating point may be determined based on values stored in a speed/load characteristic map. This may be referred to as the adaptive knock term. When the engine is operating in the same speed-load region again, the adaptive knock term at the speed-load operation point may be updated. In this way, the adaptive knock term may be updated during engine operation. The adaptive knock term may be monitored over a predetermined duration (e.g., time or number of engine cycles) of engine operation or predetermined distance of vehicle travel. If knocking rates increase with an increasing change in the adaptive knock term, spark plug fouling may be indicated.

Controller 12 is shown in FIG. 4 as a microcomputer including: microprocessor unit 402, input/output ports 404, read-only memory 406, random access memory 408, keep alive memory 410, and a conventional data bus. Controller 12 is shown receiving various signals from sensors coupled to engine 110, in addition to those signals previously discussed, including: engine coolant temperature (ECT) from temperature sensor 412 coupled to cooling sleeve 414; a position sensor 434 coupled to an accelerator pedal 430 for sensing accelerator pedal position (PP) adjusted by a foot 432 of a vehicle operator; a knock sensor for determining ignition of end gases; a measurement of engine manifold pressure (MAP) from pressure sensor 421 coupled to intake manifold 444; a measurement of boost pressure from pressure sensor 422 coupled to boost chamber 446; an engine position sensor from a Hall effect sensor 418 (or other variable reluctance sensor) sensing crankshaft 440 position; a measurement of air mass entering the engine from sensor 420 (e.g., a hot wire air flow meter); a measurement of intake air humidity from an intake humidity sensor 463, and a measurement of throttle position from sensor 456. Barometric pressure may also be sensed (sensor not shown but see FIG. 1) for processing by controller 12. In a preferred aspect of the present description, engine position sensor 418 produces a predetermined number of equally spaced pulses every revolution of the crankshaft from which engine speed (RPM) can be determined. Controller 12 receives signals from the various sensors of FIG. 4 and employs the various actuators of FIG. 4 to adjust engine operation based on the received signals and instructions stored on a memory of the controller.

As discussed above, in some embodiments, the engine may be coupled to an electric motor/battery system in a hybrid vehicle. The hybrid vehicle may have a parallel configuration, series configuration, or variation or combinations thereof.

During operation, each cylinder within engine 110 typically undergoes a four stroke cycle: the cycle includes the intake stroke, compression stroke, expansion stroke, and exhaust stroke. During the intake stroke, generally, the exhaust valve 454 closes and intake valve 452 opens. Air is introduced into combustion chamber 201 via intake manifold 444, and piston 436 moves to the bottom of the cylinder so as to increase the volume within combustion chamber 201. The position at which piston 436 is near the bottom of the cylinder and at the end of its stroke (e.g., when combustion chamber 201 is at its largest volume) is typically referred to by those of skill in the art as bottom dead center (BDC). During the compression stroke, intake valve 452 and exhaust valve 454 are closed. Piston 436 moves toward the cylinder head so as to compress the air within combustion chamber 201. The point at which piston 436 is at the end of its stroke and closest to the cylinder head (e.g., when combustion chamber 201 is at its smallest volume) is typically referred to by those of skill in the art as top dead center (TDC). In a process hereinafter referred to as injection, fuel is introduced into the combustion chamber. In a process hereinafter referred to as ignition, the injected fuel is ignited by known ignition means such as spark plug 492, resulting in combustion. During the expansion stroke, the expanding gases push piston 436 back to BDC. Crankshaft 440 converts piston movement into a rotational torque of the rotary shaft. Finally, during the exhaust stroke, the exhaust valve 454 opens to release the combusted air-fuel mixture to exhaust manifold 448 and the piston returns to TDC. Note that the above is described merely as an example, and that intake and exhaust valve opening and/or closing timings may vary, such as to provide positive or negative valve overlap, late intake valve closing, or various other examples.

Turning to FIG. 5, an exemplary parking assist system 500 employing the use of an ultrasonic sensor 585 is schematically shown. The system 500 includes components of a typical vehicle including a powertrain control module 508 illustrated as a combined control unit consisting of the controller 12 and transmission control unit 510. The system 500 further includes one or more ultrasonic sensor(s) 585, mounted on the vehicle in various locations, and configured to provide inputs to a parking assistance module 505. For example, ultrasonic sensors may be placed on a front, a side, a rear, or any combination of the front, rear, and/or side of the vehicle. Such a system 500 described in this disclosure is generally applicable to various types of vehicles, including small or large cars, trucks, vans, SUV's, etc., that may employ an ultrasonic sensor.

The term "power train" refers to a power generating and delivery system that includes an engine and a transmission, and is used as a drive system in an automotive vehicle. The power train control module 508 performs engine and transmission control operations using a controller 12 and a transmission control unit 510, respectively. The controller 12 detects data from various portions of the engine and may adjust fuel supply, ignition timing, intake airflow rate, and various other known engine operations, as discussed above with regard to FIG. 4. The transmission control unit 510 detects engine load and vehicle speed to decide a gear position to be established in the transmission. For the purpose of description, FIG. 5 depicts only a few components of the power train control module 508. Those skilled in the art, however, will understand that the power train control module 508 may be operatively coupled to a number of sensors, switches, or other known devices to gather vehicle information and control various vehicle operations.

The parking assistance module 505 provides capabilities such as auto-parking, parallel parking, obstacle identification, and so on, resulting in a convenient or completely automatic parking process. For example, using the parking assistance module 505, the vehicle may steer itself into a parking space with little or no input from the driver. In that process the module detects and warns about objects that pose an impact risk. Detection and warning are performed by a number of sensors, such as the ultrasonic sensor 585, which cooperate to determine the distance between the vehicle and surrounding objects. However, as will be discussed in further detail below, humidity and temperature may be noise factors contributing to operational use of the ultrasonic sensor.

The ultrasonic sensor 585 may detect obstacles on either side, in the front, or the rear of the vehicle, and vehicle modules, such as a steering wheel module (not shown), brake system (not shown), parking assistance module (505), etc., may utilize such information. Thus, while the one or more ultrasonic sensor(s) 585 are illustrated coupled to the parking assistance module, such a depiction is for illustrative purposes only, and is not meant to be limiting. For the sake of brevity, however, in-depth description of other potential uses of one or more ultrasonic sensor(s) will not be discussed herein. However, it may be understood that uses of the ultrasonic sensor(s) other than parking assistance may be utilized according to the methods described herein, without departing from the scope of the present disclosure.

The one or more ultrasonic sensor(s) 585 may be configured to include a transmitting (sending) means, adapted to transmit ultrasonic waves, and a receiving means, adapted to receive the waves reflected from an object in the vicinity of the vehicle, such as obstacle 520. A transit time comprising a time between transmitting and receiving the ultrasonic wave signal may be determined, and a distance between the sensor and the obstacle (for example) may be indicated based on the formula $d=t*c/2$, where c is the speed of sound and t is the transit time. This distance information may then be provided to the parking assistance module 505 (or other relevant module), for example. Such object detection capabilities of ultrasonic sensors are well known to those skilled in the art and will not be discussed in detail in the present disclosure.

As discussed above, operational use of the one or more ultrasonic sensors 585 may be subject to noise factors. For example, ultrasonic sensor signal attenuation may be a function of humidity level. Thus, for vehicles without a dedicated humidity sensor (e.g. 198), compensating for humidity may be challenging. Further, even for vehicles with a dedicated humidity sensor, if the humidity sensor is not functioning as desired, then other means may be desired for compensating humidity.

Turning now to FIG. 6, a high level example method 600 for retrieving data from one or more IoT weather devices, and for utilizing said data to compensate one or more sensor(s) in the vehicle and/or adjust one or more vehicle operating parameter(s), is shown.

Method 600 will be described with reference to the systems described herein and shown in FIGS. 1-5, though it should be understood that similar methods may be applied to other systems without departing from the scope of this disclosure. Method 600 may be carried out by a controller, such as controller 12 in FIGS. 2-4, and may be stored at the controller as executable instructions in non-transitory memory. Instructions for carrying out method 600 may be executed by the controller based on instructions stored on a memory of the controller and in conjunction with signals received from sensors of the vehicle system, such as the sensors described above with reference to FIGS. 1-5. The controller may employ vehicle system actuators, such as fuel injectors (e.g. 66), spark plug (e.g. 492), throttle (e.g. 482), etc., according to the method depicted below.

Method 600 begins at 605 and may include the vehicle controller sending a wireless signal to detect one or more IoT weather devices within a range of the vehicle. As an example, detecting one or more IoT weather devices within a range of the vehicle may depend on how the vehicle controller is attempting to communicate with the one or more IoT weather devices. As discussed above, the vehicle control system may attempt to communicate with the one or more IoT weather devices via Wi-Fi, Zigbee, Z-wave, Bluetooth, a type of cellular service, a wireless data transfer protocol, etc. In some examples, the vehicle controller may continuously search for IoT weather devices. In other examples, the vehicle controller may search for IoT weather devices in conjunction with vehicle location. As an example, if the vehicle is equipped with an onboard navigation system such as a GPS (e.g. 132), the vehicle controller may contain stored data related to location coordinates where preferred IoT weather devices are available. In other examples, as a vehicle travels throughout an environment, the controller may search for IoT weather devices. In such an example, when IoT weather devices are identified, or repeatedly identified, the vehicle controller may retrieve location data (e.g. coordinates) from the onboard navigation system, such that the location may be stored as a location where one or more IoT weather devices may be in a range to communicate with the vehicle controller. By identifying preferred locations of IoT weather devices, the vehicle controller may in some examples only search for IoT weather devices when the onboard navigation system indicates close proximity to said IoT weather devices.

To further elaborate, specific examples will be discussed below. Turning to FIG. 7, several potential sources for IoT weather data are illustrated. In one example, IoT weather devices may be located at the end of a vehicle assembly line. For example, during final assembly of vehicles, they can undergo many end of line procedures, including but not limited to camera calibration, wheel centering, etc. In such an example, it may be desirable to have one or more IoT weather devices available for compensating one or more vehicle sensor(s), and/or vehicle operating parameters, as will be discussed in further detail below. Thus, the vehicle controller may search for IoT weather devices upon first power-up of the controller, for example during an initial key-on event. In another end of the assembly line example, an operator or technician may use a specific code in a CAN bus to enable communication with the vehicle controller and the IoT devices at the end of the line. Such a procedure may be accomplished through onboard diagnostics, or through a specific sequence of push buttons, for example.

In another example, IoT weather devices may be located at a car dealership of the same make as the vehicle attempting to communicate with the IoT devices. In such an example, the vehicle controller may begin searching for IoT devices responsive to the onboard navigation system (e.g. GPS) indicating the vehicle is within a predetermined proximity to the dealership. In other examples where IoT weather devices may be located at a car dealership of the same make as the vehicle attempting to communicate with the IoT devices, communication between the controller and the IoT devices may be directly enabled by technicians at said dealership.

In another example, IoT weather devices may be located at a home of the owner of a vehicle. In such an example, the vehicle controller may begin searching for the home IoT device responsive to an indication from the onboard navigation system (e.g. GPS) that the vehicle is within a predetermined proximity to the home where the IoT device may be located. In further examples where IoT weather devices may be located at a home of the owner of the vehicle, the vehicle controller may additionally or alternatively begin searching for the IoT weather devices responsive to vehicle startup (e.g. key-on event), or vehicle shut-down (e.g. key-off event). However, such an example may still make use of an onboard navigation system, to ensure that the vehicle is located at the home of the owner of the vehicle, as discussed above. In still other examples where the IoT weather devices may be located at the home of the owner of the vehicle, the vehicle controller may attempt to initiate communication with the IoT weather devices responsive to vehicle operator initiation. For example, a software application may be installed on a vehicle operator's cellular device, or other personal computing device, such that the vehicle operator may request the vehicle controller to initiate an attempt to communicate with the IoT weather devices located at the home of the vehicle operator. Additionally or alternatively, a vehicle operator may request the vehicle controller to initiate an attempt to communicate with the IoT weather devices located at the home of the vehicle operator via inputting such a request into a vehicle instrument panel (e.g. 196), which may in some examples be configured with a human machine interface (HMI) with options for initiating communication with IoT devices.

Other examples, as alluded to above, may include any IoT weather device-enabled facility. Such examples may include a dealership that sells vehicles that are not the same make as the vehicle attempting to communicate with the IoT weather devices (e.g. a dealership not the same make as the make of the vehicle). Another example may include a home, where the owner of said home is different from the owner of the vehicle attempting to communicate with the IoT weather devices. In such examples, the vehicle may continuously, or periodically, attempt to communicate with IoT devices, and when a IoT weather device source is discovered or located, the vehicle may initiate communication with said device.

Still a further example may include a situation where the vehicle is navigating through a general area, where the vehicle controller may potentially communicate with a number of IoT weather devices. In such an example, as will be discussed in further detail below, data from a plurality of said IoT weather devices may comprise crowdsourced data, which may be processed via the vehicle controller (e.g. via a probabilistic Bayesian filter) to determine the highest likelihood measurement of one or more parameters from the IoT weather devices.

Returning to FIG. 6, any one of the above examples may constitute a situation where the vehicle controller sends a wireless signal to detect one or more IoT weather devices, as discussed. Accordingly, proceeding to 610, method 600 may include indicating whether one or more IoT weather devices are detected via the vehicle controller. If, at 610, the vehicle controller does not detect any IoT weather devices, method 600 may proceed to 615. At 615, method 600 may include maintaining current vehicle operating conditions. For example, if the vehicle is in operation, the engine (e.g. 110), HVAC system (e.g. 175), etc., may be maintained in their current operational state. In other examples, if the vehicle is not in operation, the vehicle may be maintained off. Method 600 may then end.

Returning to 610, if one or more IoT weather devices are detected, method 600 may proceed to 620. At 620, method 600 may include determining a confidence level in the IoT weather device source. Determining a confidence level in the IoT weather device source may be accomplished via a lookup table, such as the lookup table depicted at FIG. 7. More specifically, such a lookup table may include information as to the source of the detected IoT weather device, and the confidence level in said source. Turning to FIG. 7, for example, end of the line (e.g. end of assembly line) IoT weather devices may comprise an IoT data source with a high confidence level, as the operational state of the IoT weather devices at the end of the line may be carefully maintained by technicians working on said line. Similarly, IoT data sources from a dealership constituting the same make as the make of the vehicle attempting to communicate with the IoT weather device, may comprise an IoT data source with a high confidence level.

In another example, however, an IoT data source located at a home of the vehicle operator may be less reliable than either the end of the line IoT weather devices, or IoT weather devices from a dealership with the same make as the vehicle attempting to communicate with the IoT weather devices. In other words, a medium level of confidence may be attributed to IoT weather devices located at a home of the vehicle operator.

In yet another example, an IoT data source may be located at an IoT-enabled facility, which may constitute any number of facilities or locations which do not include an end of an assembly line, a dealership of the same make as the vehicle attempting to communicate with IoT weather devices, or a home of an operator of the vehicle that is attempting to communicate with the IoT weather devices. For example, such an IoT-enabled facility may include a dealership that differs from the make of the vehicle attempting to communicate with IoT weather devices, a home that does not comprise a home of the operator of the vehicle attempting to communicate with IoT weather devices, etc. In such examples, the IoT weather devices may be even less reliable, constituting a low confidence level.

In still another example, as discussed above, an IoT data source may comprise crowdsourced data. In such an example, data from a plurality of IoT weather devices may be processed (e.g. via a Bayesian filter) to determine a confidence level in the measurement from the IoT weather devices. For example, based on the data combined from the plurality of IoT weather devices, a confidence level for various parameters of the IoT weather device may be determined. As an example, it may be determined that a particular humidity value from the crowdsourced data is associated with high, medium, or low confidence. Other examples, which will be discussed in further detail below, may comprise outside air temperature, barometric pressure, etc., where confidence values based on crowdsourced data may be assigned to readings from the IoT weather devices. In some examples, the IoT weather device itself (e.g. IoT source) may be associated with a high, medium, or low confidence value.

Thus, returning to FIG. 6, as discussed above, at 620, method 600 may include determining a confidence level in the IoT weather data source, which may include the vehicle controller querying a lookup table, such as the lookup table depicted at FIG. 7.

Responsive to a confidence level being determined at 620, method 600 may proceed to 625. At 625, method 600 may include indicating whether conditions are met for retrieving IoT data. Whether conditions are met for retrieving IoT data will be discussed in substantial detail below with regard to FIGS. 7-12. Briefly, whether conditions are met may be a function of one or more of the confidence level in the IoT data source, a difference between measurements from the IoT weather device and sensor(s) of the vehicle (where the sensor(s) are included in the vehicle), etc. Such information may be stored at the vehicle controller in the lookup tables illustrated in FIGS. 7-12. FIG. 7 has been discussed above, and relates to determining confidence values in the various IoT data sources indicated. FIGS. 8-12 include lookup tables that may be stored at the vehicle controller to enable the controller to determine how to use data from the IoT weather devices, based at least in part on confidence level in the various sources of IoT weather devices, as will be discussed below.

At 625, if conditions are not indicated to be met for retrieving IoT data, method 600 may proceed to 630. At 630, method 600 may include not retrieving data from the IoT weather device identified at step 610. Method 600 may then proceed to 645, and may include updating vehicle operating parameters. For example, updating vehicle operating parameters at 645 may include setting a flag at the vehicle controller, indicating that one or more IoT weather devices were identified via the vehicle controller, but that conditions were not met for retrieving data from the one or more IoT weather devices. Method 600 may then end.

Returning to step 625, responsive to an indication that conditions are met for retrieving the IoT data from the IoT weather devices identified at step 620 of method 600, method 600 may proceed to 635. At 635, method 600 may include retrieving data from the IoT weather devices. In other words, with the vehicle controller communicatively coupled to the IoT weather devices, data from the IoT weather devices may be wirelessly transmitted to the vehicle controller. As will be discussed in detail below, such information may comprise humidity data, barometric pressure data, air temperature data, etc.

Proceeding to step 640, method 600 may include compensating one or more vehicle sensor(s), and/or adjusting one or more vehicle operating conditions or parameters, based on the retrieved data from the IoT weather devices. For example, the vehicle controller may include one or more lookup tables comprising information as to what sensor(s) may be compensated, and what vehicle operating parameters may be updated/adjusted, based on the retrieved data from the IoT weather devices. In some examples, as will be discussed below with regard to FIGS. 8-12, said lookup tables may further include information as to what sensor(s) may be compensated, and what vehicle operating parameters may be updated/adjusted, depending on a confidence level of the IoT weather device source, as discussed above.

Briefly, sensor(s) that may be compensated via data retrieved from an IoT device may include an exterior humidity sensor (e.g. 198) (where included), an intake humidity sensor (e.g. 463), a dedicated barometric pressure (BP) sensor (e.g. 153) (where included), an outside air temperature (OAT) sensor (e.g. 154), an ultrasonic sensor (e.g. 585), and/or an exhaust gas oxygen sensor (e.g. 426, 486).

In some examples, vehicle operating parameters may be adjusted responsive to one or more sensor(s) being compensated via the IoT weather device. For example, responsive to an exterior humidity sensor (e.g. 198) being compensated, an ultrasonic sensor (e.g. 585) may be compensated for humidity, such that the ultrasonic sensor is more accurate. Similarly, responsive to an OAT sensor (e.g. 154) being compensated, the ultrasonic sensor (e.g. 585), may be compensated for temperature, such that the ultrasonic sensor is more accurate. However, as discussed above, in some examples an exterior humidity sensor may not be included in the vehicle system. In such an example, humidity measurements and/or temperature measurements directly from the IoT weather device may be utilized to compensate the ultrasonic sensor (e.g. 585).

In some examples, an intake humidity sensor (e.g. 463) may be compensated based on data from an IoT weather device, as will be discussed further below. In such an example, engine operation may be adjusted based on the compensated intake humidity sensor, such that engine operation and fuel economy may be improved.

In still other examples, a dedicated BP sensor (e.g. 153) may be compensated based on data from an IoT weather device, as will be discussed further below. In such an example, a compensated BP sensor may be utilized to adjust engine operation, which may result in improved operation and control over the engine system, and increased fuel economy. However, in some examples, the vehicle system may not include a dedicated BP sensor (e.g. 153). In such cases, the vehicle system may utilize data regarding BP directly from the IoT weather device to adjust and optimize engine operation. In still other examples, vehicles without a dedicated BP sensor, or vehicles with a dedicated BP sensor that is not functioning as desired, a control strategy may default to a modeled approach which uses the intake valve and temperature to determine barometric pressure, as is known in the art. However, such a model may be less accurate than a dedicated BP sensor. Thus, in some examples, pressure data from an IoT weather devices may be utilized to calibrate errors indicated in the barometric pressure model.

Other examples may include using the data from the IoT weather device directly, or via a compensated BP sensor, to compensate a first exhaust oxygen sensor (e.g. 426) and/or a second exhaust oxygen sensor (e.g. 486). By compensating the one or more exhaust oxygen sensor(s), engine operation may be improved, for example.

Thus, at step 640, method 600 may include compensating one or more sensor(s), and adjusting one or more vehicle operation condition(s) based on retrieved data from the IoT weather device. Responsive to the one or more sensor(s) being compensated, and one or more vehicle operating parameter(s) being adjusted, method 600 may proceed to 645.

At 645, method 600 may include updating vehicle operating parameters. For example, any vehicle operating parameters that may be impacted by one or more sensor(s) being compensated, may be updated to reflect the compensated sensor measurement(s). Furthermore, any vehicle system componentry that may be impacted by the adjustment(s) to the one or more vehicle operating condition(s), may be updated to reflect the adjustment(s). Method 600 may then end.

Turning now to FIG. 8, an example lookup table 800 comprising information as to the one or more vehicle sensor(s) which may be compensated based on IoT weather device data, as well as vehicle operating parameters that may be adjusted, is shown. More specifically, example lookup table 800 may be accessed via the vehicle controller responsive to an indication that the identified IoT weather device is located at the end of a vehicle assembly line, and as such, a confidence level in the identified IoT weather device may be determined to be a high confidence level. As discussed above, in some examples an onboard navigation system (e.g. GPS) may be utilized to indicate a source of one or more IoT weather devices.

Accordingly, lookup table 800 may include column 805, indicating a location of an IoT data source, and column 810, indicating a confidence level in the identified IoT data source. Lookup table 800 may further include column 815, indicating conditions whereby one or more vehicle sensor(s) (where included in the vehicle) may be compensated via the IoT data. Lookup table 800 further includes column 820, indicating conditions whereby an ultrasonic sensor may be compensated via the IoT data. Lookup table 800 further includes column 825, indicating conditions whereby a vehicle engine may be adjusted as a function of the data retrieved from the IoT weather device. Lookup table 800 further includes column 830, indicating conditions whereby an oxygen sensor (e.g. exhaust gas oxygen sensor) may be compensated via the IoT data.

As discussed above, an IoT weather device source identified via the vehicle controller at the end of the assembly line may comprise a high confidence IoT data source. Accordingly, one or more of the exterior humidity sensor (e.g. 198) (where included), intake humidity sensor (e.g. 463), OAT sensor (e.g. 154), and/or dedicated BP sensor (e.g. 153) (where included) may be compensated for via the data retrieved from the IoT weather device, responsive to an indication that the particular sensor reading is beyond a first threshold from the IoT weather device reading. More specifically, the exterior humidity sensor (where included) may be compensated responsive to an indication that the exterior humidity sensor (where included) reading differs from a humidity reading from the IoT weather device by a first threshold amount. Similarly, an intake humidity sensor may be compensated responsive to an indication that the intake humidity sensor reading differs from a humidity reading from the IoT weather device by the first threshold amount. The OAT sensor may be compensated responsive to an indication that the OAT sensor reading differs from a temperature reading from the IoT weather device by the first threshold amount. Finally, the BP sensor (where included) may be compensated responsive to an indication that the BP sensor reading differs from a BP reading from the IoT weather device by the first threshold amount.

As the IoT data source comprises a high confidence IoT data source, IoT data retrieved from the IoT weather device may be utilized to compensate the ultrasonic sensor (e.g. 585). Briefly, ultrasonic sensor(s) may be affected by noise factors such as temperature and humidity. For example, temperature is known to affect the speed of sound, while humidity is known to have an influence on sound attenuation. Thus, without accurate information as to the outside air temperature, and humidity, ultrasonic sensor function may be degraded. Thus, it may be desirable to compensate the ultrasonic sensor via data retrieved from the IoT weather device related to temperature, and humidity.

Thus, in examples where the vehicle includes an exterior humidity sensor (e.g. 198), then the exterior humidity sensor may be first compensated via data on humidity retrieved from the IoT weather device. Subsequently, the ultrasonic sensor may be compensated, as a function of the compensated exterior humidity sensor. Alternatively, in examples where the vehicle system does not include an exterior humidity sensor, then the ultrasonic sensor may be compensated directly from the humidity value received from the IoT weather device.

Similarly, in examples where the vehicle includes an OAT sensor (e.g. 154), then the OAT sensor may be compensated via data on temperature retrieved from the IoT weather device, prior to the ultrasonic sensor being compensated as a function of the compensated OAT sensor. If, for any reason, the vehicle system does not include an OAT sensor, then the ultrasonic sensor may be compensated directly from the temperature value received from the IoT weather device.

Continuing on, as discussed above, column 825 of lookup table 800 includes information as to whether IoT data from the identified IoT weather device may be utilized to adjust engine operation. As the IoT data source comprises an end of an assembly line source where confidence in the source is high, IoT data may be utilized to improve engine operation. In some examples, as confidence in the IoT data source is high, data retrieved from the IoT weather device may be directly utilized to adjust engine operation, for example in cases where one or more sensor(s) are not included in the vehicle system. However, in other examples, vehicle sensor(s) such as exterior humidity sensor, intake humidity sensor, OAT sensor, and/or BP sensor may be first compensated via the data received from the IoT weather device, and engine operation may be subsequently adjusted responsive to the compensated sensor value(s). In some examples, engine operation may be adjusted via a combination of data received directly from the IoT weather device, and via sensors compensated via data received from the IoT weather device.

As one example, by correcting ambient air temperature from a high confidence source, models for intake air temperature may be improved. Such an improvement to intake air temperature accuracy may allow the ability of the vehicle controller to inject more or less fuel to maintain intended output power. Such an optimization may improve fuel economy in the vehicle.

As another example, as discussed above, some vehicle systems may not include a dedicated BP sensor, and instead may rely on modeled BP. In such examples where the source of the IoT weather device is at the end of an assembly line, by utilizing data received from the IoT weather device related to BP, such a model may achieve an initial calibration by comparing itself with the data received from the IoT device. In other examples, wherein the vehicle includes a dedicated BP sensor, and where the dedicated BP sensor is compensated via data related to BP from the IoT weather device, adjustments to engine operation may be made as a function of the compensated dedicated BP sensor. For example, the compensated BP value may be utilized to adjust engine controlling parameters such as the desired A/F ratio, spark timing, or desired EGR level.

As another example, engine operation may be adjusted as a function of an accurate humidity determination. For example, engine operation may be adjusted as a function of a compensated exterior humidity sensor, where the vehicle includes such a sensor. Alternatively, if the vehicle does not include an exterior humidity sensor, then engine operation may be adjusted based on a humidity value received directly from the IoT weather device. Such an improvement in accuracy of a humidity measurement may allow the engine to take in additional air to maintain intended output power, which may improve fuel economy. Taking in additional air may be regulated by the vehicle controller regulating an opening of a throttle (e.g. throttle 462, or AIS throttle 482).

Continuing on, column 830 of lookup table 800 includes information as to whether the IoT data from the identified IoT weather device may be utilized to compensate an oxygen sensor, for example one or more exhaust gas oxygen sensor(s). Because the IoT data source comprises an end of assembly line IoT weather device, and is thus a high confidence source of data, the one or more oxygen sensor(s) may be compensated as a function of a BP measurement retrieved from the IoT weather device. For example, the one or more oxygen sensor(s) may utilize high confidence BP data retrieved from the IoT weather device to apply a gain correction to the sensor output. Such an action may reduce sensor part-to-part variability, for example.

Turning now to FIG. 9, an example lookup table 900 comprising information as to the one or more vehicle sensor(s) which may be compensated based on IoT weather device data, as well as vehicle operating parameters that may be adjusted, is shown. More specifically, example lookup table 900 may be accessed via the vehicle controller responsive to an indication that the identified IoT weather device is located at a dealership, where said dealership is of the same make as the vehicle attempting to communicate with the IoT weather device. As an example, table 900 may be accessed responsive to a Ford vehicle establishing communication with an IoT weather device at a Ford dealership. In such an example wherein the identified IoT weather device is located at a dealership of the same make as the vehicle, a confidence level in the identified IoT weather device may be determined to be a high confidence level.

Accordingly, lookup table 900 may include column 905, indicating a location of an IoT data source, and column 910, indicating a confidence level in the identified IoT data source. Lookup table 900 may further include column 915, indicating conditions whereby one or more vehicle sensor(s) (where included in the vehicle) may be compensated via the IoT data. Lookup table 900 may further include column 920, indicating conditions whereby an ultrasonic sensor may be compensated via the IoT data. Lookup table 900 further includes column 925, indicating conditions whereby a vehicle engine may be adjusted as a function of the data retrieved from the IoT weather device. Lookup table 900 further includes column 930, indicating conditions whereby an oxygen sensor (e.g. exhaust gas oxygen sensor) may be compensated via the IoT data.

It may be understood that as the IoT data source comprises a data source of a high confidence level, lookup table 900 is substantially equivalent to lookup table 800. As lookup table 800 has been discussed in detail above, for brevity such a description will not be reiterated here. However, it may be understood that all aspects discussed with regard to lookup table 800 above, may be applied to table 900, without departing from the scope of this disclosure.

Turning now to FIG. 10, an example lookup table 1000 comprising information as to the one or more vehicle sensor(s) which may be compensated based on IoT weather device data, as well as vehicle operating parameters that may be adjusted, is shown. More specifically, example lookup table 1000 may be accessed via the vehicle controller responsive to an indication that the identified IoT weather device is located at a home of an operator of the vehicle. In such an example wherein the identified IoT weather device is located at a personal home of an operator of the vehicle, a confidence level in the identified IoT weather device may be determined to be a medium confidence level. It may be understood that the medium confidence level depicted at FIG. 10 is of a lower confidence than the high confidence level depicted at FIGS. 8-9.

Similar to the lookup tables depicted at FIGS. 8-9, lookup table 1000 may include column 1005, indicating a location of an IoT data source, and column 1010, indicating a confidence level in the identified IoT data source. Lookup table 1000 may further include column 1015, indicating conditions whereby one or more vehicle sensor(s) (where included in the vehicle) may be compensated via the IoT data. Lookup table 1000 may further include column 1020, indicating conditions whereby an ultrasonic sensor may be compensated via the IoT data. Lookup table 1000 further includes column 1025, indicating conditions whereby a vehicle engine may be adjusted as a function of the data retrieved from the IoT weather device. Lookup table 1000 further includes column 1030, indicating conditions whereby an oxygen sensor (e.g. exhaust gas oxygen sensor) may be compensated via the IoT data.

As discussed above, an IoT weather device source identified via the vehicle controller at a personal home of an operator of the vehicle may comprise a medium confidence IoT data source. Accordingly, one or more of the exterior humidity sensor (e.g. 198) (where included), intake humidity sensor (e.g. 463), OAT sensor (e.g. 154), and/or dedicated BP sensor (e.g. 153) (where included) may be compensated for via the data retrieved from the IoT weather device, responsive to an indication that the particular sensor reading is beyond a second threshold from the IoT weather device reading. It may be understood that the second threshold may comprise a "looser" threshold as compared to the first threshold described above with regard to FIGS. 8-9. In other words, a smaller difference between a sensor reading and an IoT reading may result in the one or more sensor(s) of FIGS. 8-9 at columns 815 and 915, respectively, being compensated as a result of the first threshold, whereas a bigger difference (comparably) between the one or more sensor(s) of FIG. 10 at column 1015 and an IoT reading may result in the one or more sensor(s) of FIG. 10 at column 1015 being compensated as a result of the second threshold. Such a second threshold may serve to ensure that the one or more sensor(s) depicted at column 1015 of FIG. 10 are only compensated for if value(s) of the said sensor(s) differ from the personal IoT weather device readings by an amount surpassing the larger difference.

In an example where the one or more sensor(s) readings are beyond the second threshold, said sensor(s) may be compensated substantially equivalently to that described above for FIGS. 8-9. Briefly, one or more of the exterior humidity sensor (e.g. 198) (where included), intake humidity sensor (e.g. 463), OAT sensor (e.g. 154), and/or dedicated BP sensor (e.g. 153) (where included) may be compensated for via the data retrieved from the IoT weather device, responsive to an indication that the particular sensor reading is beyond a second threshold from the IoT weather device reading.

Continuing on, as the identified IoT weather device with regard to FIG. 10 comprises an IoT weather device with a medium confidence level, a vehicle ultrasonic sensor (e.g. 585) may utilize such IoT data with additional reservations. As one example, if a threshold duration has passed since the ultrasonic sensor was compensated via a more trusted, or higher confidence, IoT weather device, then the vehicle controller may ignore such IoT data, and may thus not compensate the ultrasonic sensor (e.g. 585) based on said IoT data. More specifically, as discussed above, ultrasonic sensor accuracy may be a function of temperature and humidity. Thus, for medium confidence IoT data, such as that described with regard to FIG. 10, both temperature and humidity data may not be utilized to compensate the ultrasonic sensor, responsive to a threshold duration passing since a more trusted IoT weather device was utilized to compensate the ultrasonic sensor.

In other words, medium confidence IoT weather device data may be utilized to compensate an ultrasonic sensor (e.g. 585), as long as the threshold duration has not elapsed. In some examples, using IoT weather device data to compensate the ultrasonic sensor may comprise first compensating an exterior humidity sensor (e.g. 198) via humidity data retrieved from the IoT weather device, if the vehicle is equipped with such an exterior humidity sensor, and further responsive to the exterior humidity sensor measurement being beyond the second threshold from the IoT weather device humidity determination. In such an example, the ultrasonic sensor may subsequently be compensated via the compensated exterior humidity sensor. Alternatively, in a case where the vehicle is not equipped with an exterior humidity sensor, IoT weather device data may be utilized directly from an identified IoT weather device to compensate the ultrasonic sensor, provided the threshold duration has not elapsed.

In another example, IoT weather device temperature data may be utilized to compensate an OAT sensor (e.g. 154), and then the ultrasonic sensor may be compensated via the compensated OAT sensor. Such an example may occur responsive to an indication that the OAT sensor temperature measurement is beyond the second threshold from the IoT weather device temperature indication, wherein the OAT sensor may thus be compensated via the IoT weather device temperature data. In other examples, temperature data from the IoT weather device may be utilized directly by the ultrasonic sensor, for ultrasonic sensor compensation, provided that the threshold duration has not elapsed since the ultrasonic sensor was previously compensated via a higher confidence IoT weather device.

In still another example, a vehicle ultrasonic sensor may additionally or alternatively be compensated via data retrieved from a medium confidence IoT weather device as long as a number of times that the ultrasonic sensor has been compensated via medium confidence IoT weather devices remains below a threshold number, and/or responsive to the predetermined threshold duration not elapsing. As an example, for an ultrasonic sensor utilizing temperature and humidity data for compensating the ultrasonic sensor via one or more medium confidence IoT weather devices, as the number of times the ultrasonic sensor is compensated via medium confidence IoT weather data, an overall confidence in the ultrasonic sensor measurement may decrease. In some examples, the vehicle controller may track the number of times and confidence level for which an ultrasonic sensor has been compensated via IoT weather devices. If it is indicated that the number of times that the ultrasonic sensor has been compensated for via medium confidence IoT data is beyond the threshold number, then the IoT weather device may be ignored for compensating the ultrasonic sensor until a high confidence IoT weather device is identified via the vehicle controller.

Continuing on with regard to lookup table 1000, column 1025 includes information as to whether IoT data from the identified IoT weather device may be utilized to adjust engine operation. As the IoT data comprises a medium confidence data source, similar to the ultrasonic sensor discussed above with regard to medium confidence data, IoT data may only be utilized from medium confidence data source(s) if a threshold duration has not passed since engine operation has been adjusted based on a higher confidence data source. In some examples, the threshold duration may be the same as the threshold duration discussed above with regard to whether the ultrasonic sensor may utilize information from a medium confidence IoT data source. However, in other examples, the threshold duration may not be the same as the threshold duration discussed above with regard to whether the ultrasonic sensor may utilize information from a medium confidence IoT data source.

Similar to that discussed above, engine operation may additionally or alternatively be adjusted via data retrieved from a medium confidence IoT weather device as long as a number of times that engine operation has been adjusted via medium confidence data remains below a threshold number. Such a threshold number may be the same as, or different from, the threshold number discussed above with regard to ultrasonic sensor(s) being compensated via medium confidence IoT data. For example, as the number of times the engine is adjusted via data retrieved from a medium confidence IoT weather device increases, overall confidence in engine operation may decrease. Thus, if it is indicated that the number of times that engine operation has been adjusted based on medium confidence IoT weather device data is beyond the threshold number, then the IoT weather device may be ignored for compensating the engine until a high confidence IoT weather device is identified via the vehicle controller.

As discussed above, in some examples data retrieved from the IoT weather device may be directly utilized to adjust engine operation, however in other examples, vehicle sensor(s) such as exterior humidity sensor, intake humidity sensor, OAT sensor, and/or BP sensor may be first compensated via the data received from the IoT weather device, and engine operation may be subsequently adjusted responsive to the compensated sensor value(s). In still other examples, engine operation may be adjusted via a combination of data received directly from the IoT weather device, and via sensors compensated via data received from the IoT weather device.

The types of adjustments to engine operation that may be made responsive to data retrieved from an IoT weather device have been discussed in detail above with regard to FIG. 8. Briefly, one example includes improving models for intake air temperature, which may improve fuel economy. Another example includes adjusting engine controlling parameters such as desired A/F ratio, spark timing, or desired EGR level, based at least in part on pressure data retrieved from one or more IoT weather devices. In still another example, an accurate knowledge of humidity obtained via one or more IoT weather devices may thus enable the engine to take in additional air to maintain intended output power, which may improve fuel economy.

Continuing on with regard to lookup table 1000, column 1030 includes information as to whether the IoT data from the medium confidence IoT weather device may be utilized to compensate an oxygen sensor, for example one or more exhaust gas oxygen sensor(s). A substantially equivalent procedure may be utilized for compensating one or more oxygen sensor(s) as that described above with regard to an ultrasonic sensor and engine operating parameters being compensated, or adjusted, respectively, via medium confidence IoT weather device data. For brevity, all aspects will not be repeated here, but it may be understood that the one or more oxygen sensor(s) may be compensated for based on pressure data retrieved from a medium confidence IoT weather device only if a threshold duration has not passed since the one or more oxygen sensor(s) were compensated via higher confidence IoT weather device data. In some examples, the threshold duration may be the same as the threshold duration discussed above with regard to whether the ultrasonic sensor and/or engine may utilize information from a medium confidence IoT data source. However, in other examples, the threshold duration may be different from the threshold duration for the ultrasonic sensor and/or engine with regard to utilizing medium confidence IoT weather device data.

Similar to that discussed above, one or more oxygen sensor(s) may additionally or alternatively be adjusted via data received from a medium confidence IoT weather device as long as a number of times that the one or more oxygen sensor(s) have been compensated remains below a threshold number. Such a threshold number may be the same as, or different from, the threshold number discussed above with regard to ultrasonic sensor(s) and/or engine operation being compensated for or adjusted, respectively, based on medium confidence IoT weather data. In a case where the one or more oxygen sensor(s) may be compensated via pressure data retrieved from the IoT weather device, it may be understood that the vehicle controller may apply a gain correction to the one or more oxygen sensor(s) output, which may reduce part-to-part variability, as discussed above.

Turning now to FIG. 11, an example lookup table 1100 comprising information as to the one or more vehicle sensor(s) which may be compensated based on IoT weather device data, as well as vehicle operating parameters that may be adjusted, is shown. More specifically, example lookup table 1100 may be accessed via the vehicle controller responsive to an indication that the identified IoT weather device is located either at a home of an individual that does not include the owner or operator of the vehicle. Another example may include a situation where the identified IoT weather device is located at a dealership that does not comprise the same make as the vehicle. Such examples are meant to be illustrative. For example, other possibilities such as IoT weather devices from companies, gas stations, grocery stores, etc., may be included. In such examples, a confidence level in the identified IoT weather device may be determined to be a low confidence level. It may be understood that the low confidence level depicted at FIG. 11 is of a lower confidence level than the high confidence level depicted at FIGS. 8-9, and of a lower confidence level than the medium confidence level depicted at FIG. 10.

Similar to the lookup tables depicted at FIGS. 8-10, lookup table 1100 may include column 1105, indicating a location of an IoT data source, and column 1110, indicating a confidence level in the identified IoT data source. Lookup table 1100 may further include column 1115, indicating conditions whereby one or more vehicle sensor(s) (where included in the vehicle) may be compensated via the IoT data. Lookup table 1100 may further include column 1120, indicating conditions whereby an ultrasonic sensor may be compensated via the IoT data. Lookup table 1100 further includes column 1125, indicating conditions whereby a vehicle engine may be adjusted as a function of the data retrieved from the IoT weather device. Lookup table 1100 further includes column 1130, indicating conditions whereby an oxygen sensor (e.g. exhaust gas oxygen sensor) may be compensated via the IoT data.

As discussed above, an IoT weather device source identified via the vehicle controller at a home other than a home of the vehicle operator (e.g. friend's house), or other IoT-enabled facility such as a dealership not of the same make as the vehicle, may comprise a low confidence IoT data source. Accordingly, one or more of the exterior humidity sensor (e.g. 198) (where included), intake humidity sensor (e.g. 463), OAT sensor (e.g. 154), and/or dedicated BP sensor (e.g. 153) (where included) may be compensated for via the data retrieved from the IoT weather device, responsive to an indication that the particular sensor reading is beyond a third threshold from the IoT weather device reading. It may be understood that the third threshold may comprise a "looser" threshold as compared to both the first threshold described above with regard to FIGS. 8-9, and the second threshold described above with regard to FIG. 10.

Thus, much of the time, a vehicle controller may ignore such low confidence IoT weather devices, as the exterior sensor, intake humidity sensor, OAT sensor, and/or dedicated BP sensor may not be outside, or beyond, the third threshold. However, there may be cases wherein one or more of said sensor(s) readings may be outside, or beyond the third threshold, at which point such sensor(s) may be compensated.

As discussed above, ultrasonic sensor(s) may rely on accurate knowledge of humidity and temperature in order to function as desired. However, it may not be desired to compensate an ultrasonic sensor with low confidence IoT weather device data. Similarly, engine operation may rely on accurate knowledge of one or more of temperature, humidity, and BP. However, it may again not be desired to adjust engine operation based on low confidence IoT weather data. Still further, oxygen sensor(s) may rely on accurate knowledge of BP. However, it may again not be desired to adjust oxygen sensor function via applying a gain correction to the oxygen sensor output, responsive to data retrieved from a low confidence IoT weather device.

Thus, responsive to a low confidence IoT weather device being identified, the vehicle controller may instruct the ultrasonic sensor to ignore the low confidence IoT weather device data. Similarly, the vehicle controller may instruct the engine to maintain engine operation without adjustments, and may maintain operation of the one or more oxygen sensor(s) without adjustment/compensation, responsive to an indication that an IoT weather device comprises a low confidence data source.

As discussed above, in some examples, a vehicle may not include certain sensors, such as an exterior humidity sensor and/or a dedicated BP sensor. In such examples, rather than directly utilize IoT weather device data for ultrasonic sensor compensation, oxygen sensor compensation, or engine operation adjustments, such IoT weather device data may be ignored.

In other examples, where the vehicle is equipped with certain sensors, such as an exterior humidity sensor and/or a BP sensor, even under conditions where the said sensor(s) are beyond the third threshold, and thus may be compensated via the low confidence IoT data source, the ultrasonic sensor, engine, and oxygen sensor(s) may ignore such compensated sensors for their operation. Alternatively, in other examples, the ultrasonic sensor, engine, and oxygen sensor(s) may only utilize data from sensors such as the exterior humidity sensor, BP sensor, OAT sensor, and/or intake humidity sensor, responsive to an indication that said sensor(s) have been compensated as a result of being beyond the third threshold.

Turning now to FIG. 12, an example lookup table 1200 comprising information as to the one or more vehicle sensor(s) which may be compensated based on IoT weather device data, as well as vehicle operating parameters that may be adjusted, is shown. More specifically, example lookup table 1200 may be accessed via the vehicle controller responsive to an indication that the identified IoT data source comprises a crowd-sourced IoT data source. In other words, such an example may comprise a situation wherein the vehicle is driving through an area where a plurality of IoT weather devices are detected. In a case where a plurality of IoT weather devices are identified, it may be understood that typically such IoT weather devices would be of a low confidence value. However, the vehicle controller may receive input from the plurality of IoT weather devices, and may process said input through a probabilistic Bayesian filter, which may enable the vehicle controller to identify or determine the highest likelihood measurement. In such an example, the vehicle controller may additionally assign a confidence value to the highest likelihood measurement. For example, the highest likelihood measurement may comprise a high confidence value, a medium confidence value, or a low confidence value. Thus, upon ascribing a confidence value to said highest likelihood measurement, the vehicle sensor(s) (e.g. exterior humidity sensor, intake humidity sensor, OAT sensor, BP sensor, ultrasonic sensor, oxygen sensor(s), etc.) may be compensated/adjusted as described above, only if the highest likelihood measurement corresponds to a high confidence result. Furthermore, engine operation may be adjusted based on crowd-sourced IoT weather device data as discussed above, responsive to the highest likelihood measurement comprising a high confidence value.

Thus, similar to the lookup tables depicted at FIGS. 8-11, lookup table 1200 may include column 1205, indicating a location of an IoT data source, and column 1210, indicating a confidence level in the identified IoT data source. Lookup table 1200 may further include column 1215, indicating conditions whereby one or more vehicle sensor(s) (where included in the vehicle) may be compensated via the IoT data. Lookup table 1200 may further include column 1220, indicating conditions whereby an ultrasonic sensor may be compensated via the IoT data. Lookup table 1200 further includes column 1225, indicating conditions whereby a vehicle engine may be adjusted as a function of the data retrieved from the IoT weather device. Lookup table 1200 further includes column 1230, indicating conditions whereby an oxygen sensor (e.g. exhaust gas oxygen sensor) may be compensated via the IoT data.

In all columns 1215, 1220, 1225, and 1230, example lookup table 1200 illustrates only compensating sensor(s) or adjusting engine operation responsive to a high confidence value. In other words, the sensor(s) and engine operation may be compensated or adjusted, respectively, as described above with regard to FIGS. 8-9. Accordingly, a reiteration of the description above will not be provided here, for brevity. In a case where crowd-sourced data from a plurality of IoT weather devices is indicated to be either medium, or low confidence, the crowd-sourced data may be ignored by the sensors depicted at FIG. 11, and engine operation may be maintained without adjustments.

However, in other examples, medium and low confidence crowd-sourced data may be utilized, as discussed above with regard to FIGS. 9-10. In other words, in some cases, it may be determined that the highest likelihood IoT values are of a medium, or low, confidence level. In such cases, sensor(s) may be compensated for, with additional reservations, as discussed in detail above with regard to FIGS. 9-10. As a description of how sensor(s) and engine operation may be compensated for, and adjusted, respectively, as a function of medium or low confidence data, such a description will not be reiterated here, for brevity.

Returning to FIG. 6, step 625 determines whether conditions are met for compensating and/or adjusting vehicle operating parameters, as discussed. FIGS. 7-12 discuss various conditions whereby one or more sensor(s) may be compensated and/or vehicle operating parameters may be adjusted, depending on confidence level in IoT weather device data sources. However, an additional contingency may be imposed on whether conditions are met for compensating an intake humidity sensor (e.g. 463). Such an additional contingency will be discussed below.

An intake humidity sensor may comprise a dielectric/capacitive humidity sensor, which may in some examples be coupled with a temperature sensor and mass air flow (MAF) or mass air pressure (MAP) sensor. Such a sensor positioned in the intake of a vehicle engine may be affected by the flow of air going past it. Such air may in some examples include water vapor entrained in the intake air stream. Water vapor may be entrained in the intake air stream as a result of condensate stemming from a charge air cooler (CAC). In other examples, an intake air humidity sensor may be exposed to liquid water from a water injection system (not shown). Thus, it may be understood that if the engine is in operation, humidity measurements retrieved from one or more IoT weather devices may be significantly different than a humidity measurement via the intake humidity sensor. As such, if the intake humidity sensor were simply compensated via an IoT device under conditions where the engine is in operation (or soon after shutdown), the intake humidity sensor measurements may become degraded or incorrect. Accordingly, a method for compensating or calibrating an intake humidity sensor, will be discussed below with regard to method 1300 depicted at FIG. 13.

Turning now to FIG. 13, a high level example method 1300 for calibrating/compensating an intake humidity sensor (e.g. 463), is shown. More specifically, method 1300 may comprise a sub-method of method 600 depicted above at FIG. 6, and may include determining a threshold duration that a vehicle may be maintained in a mode where the engine is off with a transmission of the vehicle is in a park mode of operation, prior to calibrating or compensating the intake humidity sensor. In other words, method 600 may proceed through step 625, prior to initiating steps defined by FIG. 13. After completing FIG. 13, method 1300 may return to step 625, for example. By maintaining the vehicle engine off and the transmission in park for the threshold duration prior to calibrating the intake humidity sensor (e.g. 463), it may be understood that a concentration of water vapor in air in an intake manifold of the engine near the intake humidity sensor may be substantially equivalent to the concentration of water vapor in air surrounding the vehicle.

Method 1300 will be described with reference to the systems described herein and shown in FIGS. 1-4, though it should be understood that similar methods may be applied to other systems without departing from the scope of this disclosure. Method 1300 may be carried out by a controller, such as controller 12 in FIGS. 2-4, and may be stored at the controller as executable instructions in non-transitory memory. Instructions for carrying out method 1300 may be executed by the controller based on instructions stored on a memory of the controller and in conjunction with signals received from sensors of the vehicle system, such as the sensors described above with reference to FIGS. 1-4. The controller may employ vehicle system actuators according to the method depicted below.

Method 1300 may comprise a sub-method of method 600 at step 625. An enabler for method 1300 may include an indication of engine misfires, which may indicate that the intake air is very dry and that the intake humidity sensor is not recognizing the dryness of the air. For example, if the intake humidity sensor falsely indicates that humidity is low, the controller may retard spark, which may result in misfire. Thus, if misfire is detected, it may be determined whether the intake humidity sensor is reading low. Another example may include an indication of knock, wherein responsive to an indication of knock, a flag may be set to test the humidity sensor during the next engine shutdown event. Conversely, if the intake air is very humid, then engine controls may use such an opportunity to advance spark and achieve higher torque. Thus, there may be circumstances where the controller may check ignition timing against an external indication of humidity, and if the ignition timing appears too retarded given the external humidity indication, then a calibration for the intake humidity sensor may be initiated at next engine shutdown, for example.

Method 1300 begins at 1305 and may include indicating whether an engine shutoff event is indicated, and whether a transmission of the vehicle has been put into a park mode of operation. In other words, at 1305, it may be indicated as to whether the vehicle is not in operation, with the vehicle transmission in park. As an example, a key-off event may indicate an engine shutdown event.

If, at 1305, it is indicated that the engine is not shut off, and/or the transmission is not in a park mode of operation, method 1300 may proceed to 1310. At 1310, method 1300 may include maintaining current vehicle operating parameters. For example, the vehicle may in some examples be operating in an electric-only mode of operation where the engine is not being utilized to propel the vehicle (or charge an onboard energy storage device). In such an example, electric-only operation may be maintained. In other examples, the engine may be indicated to be in operation, for propelling the vehicle, or charging an onboard energy storage device. In such an example, engine operation may be maintained. Method 1300 may then end.

Returning to 1305, responsive to an indication that an engine shutdown event has occurred, and further responsive to an indication that the vehicle transmission has been placed in a park mode of operation, method 1300 may proceed to 1315. At 1315, method 1300 may include the vehicle controller retrieving current and forecast weather information from an off-board computing system (e.g. 109). Additionally or alternatively, in some examples where the vehicle includes an onboard navigation system (e.g. 132), information received from the onboard navigation system may be cross-referenced to information available via the internet to determine current and forecast weather conditions. Such information may include current and forecast information regarding precipitation, humidity, wind, temperature, etc., where such information may be utilized by method 1300 to determine a threshold duration that the engine must be off with the transmission in park mode, prior to calibrating the intake humidity sensor, as will be further discussed below.

Accordingly, responsive to retrieving current and forecast weather information at the vehicle controller at 1315, method 1300 may proceed to 1320. At 1320, method 1300 may include determining a threshold duration that the engine may be maintained off with the transmission in park. The threshold duration may be a function of the current and forecast weather information, for example. More specifically, the threshold duration may be adjusted as a function of the current and forecast weather information. For example, if it is indicated to be raining, or snowing outside, and it is further indicated that the vehicle is experiencing the rain, snow, etc. (e.g. parked outside while it is snowing, raining, etc.), then the threshold duration may be increased. In some examples, whether the vehicle is experiencing the rain/snow, etc., may be indicated via one or more onboard camera(s) (e.g. 108), and/or rain sensor(s) (e.g. 107). Alternatively, if it is indicated that the vehicle is not in an environment where the vehicle is experiencing precipitation, then the threshold duration may be decreased. Such examples are meant to be illustrative. For example, it may be understood that any environmental condition that may result in air exterior to the vehicle (e.g. surrounding the vehicle, within close proximity, or a predetermined radius, to the vehicle) comprising a concentration of water vapor substantially different than a concentration of water vapor in air near the intake humidity sensor (e.g. 463), may result in an increase in the threshold duration (e.g. until the rain/snow, etc., has stopped and where the concentration of water vapor in the air exterior to the vehicle is substantially similar to the concentration of water vapor in the air near the intake humidity sensor). While not explicitly shown, in some examples the threshold duration may be sufficiently long that calibrating the intake humidity sensor may be aborted, or postponed. For example, if the threshold duration comprises greater than 5 hours, or greater than 8 hours, or greater than 12 hours, or greater than 24 hours, then the intake humidity sensor calibration may be postponed.

Thus, it may be understood that at 1320, the vehicle controller may indicate the threshold duration, where the threshold duration may comprise a duration whereby it may be indicated that a water vapor concentration in air near the intake humidity sensor (e.g. in an intake manifold of the engine) is substantially equivalent to a water vapor concentration in air exterior to the vehicle (e.g. surrounding the vehicle). By ensuring that the concentration of water vapor in the air near the intake humidity sensor is substantially equivalent to the concentration of water vapor in the air surrounding the vehicle, accuracy of the intake humidity sensor calibration may be increased.

Said another way, the threshold duration may comprise a duration such that humidity of air in the intake manifold near the intake humidity sensor may be substantially equivalent to ambient outdoor humidity as monitored via the IoT weather device(s). The vehicle controller may include an algorithm that may determine an amount of time that the vehicle may remain in park with the engine off, in order for conditions to be met for compensating the intake humidity sensor. In some examples, the algorithm may adjust the amount of time the vehicle may remain in park with the engine off, depending on environmental conditions. Environmental conditions may be indicated to the vehicle controller via one of at least an onboard navigation system (e.g. GPS), an off-board computing system (e.g. 109), or via one or more IoT weather devices communicatively coupled to the vehicle controller. In still other examples, environmental conditions may be indicated to the vehicle controller via a cellular phone, or personal computing device, which may be communicatively coupled to the vehicle controller. In such examples as described above, after the determined period of time elapses for the environmental factors to satisfy the condition that air in the intake is the same as exterior air, then it may be indicated that conditions are met for compensating the intake humidity sensor.

In some examples, conditions may not be indicated to be met for the intake humidity sensor. Such examples may include conditions where it is indicated that it is currently snowing or raining and where it is forecast to continue raining/snowing for a duration greater than a predetermined timeframe. In a case where it is snowing or raining, the source of humidity information may report humidity information that may be significantly different from that of the intake humidity sensor, as the intake humidity sensor may be shielded from rain/snow. However, there may be some cases where it is raining/snowing outside, but where compensation of the intake humidity sensor may take place. Such examples may include a situation where it is raining/snowing outside, but where the vehicle is parked in a garage or other covered structure. Thus, in some examples, conditions being met for compensating the intake humidity sensor may include an indication that the source of IoT weather data is experiencing a similar environmental environment as the vehicle attempting to calibrate its intake humidity sensor. In some examples, such indications may be made via one or more onboard cameras (e.g. 108) and/or one or more rain sensors (e.g. 107).

Responsive to determining the threshold duration at 1320, method 1300 may proceed to 1325. At 1325, method 1300 may include indicating whether the threshold duration has elapsed. If, at 1325, it is indicated that the threshold duration has not yet elapsed, method 1300 may continue to maintain the vehicle engine off with the transmission in park, until it is indicated that the threshold duration has elapsed. In some examples, the engine may be started via a vehicle operator prior to the threshold duration elapsing. In such examples, the intake humidity calibration may be aborted.

Responsive to the threshold duration elapsing at 1325, method 1300 may return to step 625 of method 600. At 625, it may be indicated that at least one condition has been met for retrieving the IoT data and compensating the intake humidity sensor. However, whether conditions are indicated to be met may be further a function of the confidence level in the source of the IoT weather device (determined at 620), and whether an intake humidity sensor measurement is beyond a first threshold difference from a humidity measurement from the IoT weather device, beyond a second threshold difference from the humidity measurement from the IoT weather device, or beyond a third threshold difference from the humidity measurement from the IoT weather device. Such examples have been discussed in detail above, and will not be further discussed here for brevity. However, it may be understood that the lookup tables depicted at FIGS. 8-12 may be utilized to further determine whether conditions are met for calibrating the intake humidity sensor.

In some examples, prior to determining the threshold duration that the vehicle engine may remain off with the transmission in park, it may be first determined as to whether conditions are otherwise met for calibrating the intake humidity sensor, according to the method of FIG. 6 and further according to the lookup tables depicted at FIGS. 8-12. If it is otherwise indicated that the conditions for calibrating the intake humidity sensor are met, then sub-method 1300 may be utilized to further indicate when the sensor may be calibrated, responsive to an indication that the threshold duration has elapsed.

Responsive to conditions being met at 625, method 600 may proceed to 635 and may include retrieving data from the IoT weather device, as discussed above. In an example where the intake humidity sensor is being calibrated, it may be understood that the data retrieved from the IoT weather device may include at least humidity data.

Proceeding to 635, method 600 may include compensating, or calibrating the intake humidity sensor (e.g. 463). For example, the vehicle controller may adjust a gain and/or offset error of the intake humidity sensor based on the humidity data retrieved from the IoT device. In such an example, it may be understood that the intake humidity sensor value may be increased in accuracy responsive to the calibration/compensation.

In some examples, responsive to the intake humidity sensor being calibrated, engine operating parameters may be adjusted/updated. For example, with accurate knowledge of the intake humidity, an amount of air inducted into the engine may be adjusted or optimized to maintain intended output power. Such an optimization may improve fuel economy of the vehicle, for example.

Proceeding to 645, as discussed above, method 600 may include updating vehicle operating parameters. For example, any vehicle operating parameters that may be impacted by the intake humidity sensor being calibrated/compensated, may be updated to reflect the compensated sensor measurement. Method 600 may then end.

Turning now to FIG. 14, a high level example method 1400 for calibrating/compensating an interior humidity sensor (e.g. 152), is shown. The interior humidity sensor may comprise one of a dielectric or capacitive humidity sensor, for example. More specifically, method 1400 may include the vehicle controller communicating a request to a vehicle operator to compensate the vehicle's interior humidity sensor (e.g. 152) via the vehicle operator's personal computing device (e.g. 90). For example, the personal computing device may be equipped with a humidity sensor, which may be utilized to calibrate the vehicle interior humidity sensor.

Method 1400 will be described with reference to the systems described herein and shown in FIGS. 1-5, though it should be understood that similar methods may be applied to other systems without departing from the scope of this disclosure. Method 1400 may be carried out by a controller, such as controller 12 in FIGS. 2-4, and may be stored at the controller as executable instructions in non-transitory memory. Instructions for carrying out method 1400 may be executed by the controller based on instructions stored on a memory of the controller and in conjunction with signals received from sensors of the vehicle system, such as the sensors described above with reference to FIGS. 1-5. The controller may employ vehicle system actuators, such as clutch (e.g. 210), fan (e.g. 237), heater shut-off valve (e.g. 322), etc., according to the method depicted below.

Method 1400 begins at 1405 and may include the vehicle controller (e.g. 190) indicating whether conditions are met for calibrating a vehicle interior humidity sensor (e.g. 152). It may be understood that a vehicle's interior humidity may differ substantially from humidity exterior to the vehicle. Thus, calibrating a vehicle's interior humidity sensor (e.g. 152) based on exterior humidity may not be desirable. Accordingly, rather than utilizing IoT weather device data (as discussed above) to calibrate/compensate the vehicle's interior humidity sensor, a personal computing device (e.g. 90) equipped with a humidity sensor (e.g. 97) may be utilized to provide an accurate indication of interior cabin humidity, which may be utilized to compensate the vehicle's interior humidity sensor.

Accordingly, conditions being met at 1405 for conducting an interior humidity sensor calibration may include a predetermined threshold duration elapsing since a prior interior humidity sensor calibration. Conditions being met at 1405 may additionally or alternatively include an indication from the vehicle controller that the interior humidity estimation is likely degraded, and thus it is recommended to update said intake humidity estimation. In some examples, conditions being met at 1405 may additionally or alternatively include an operator request, a humidity reading from another sensor such as an outside humidity sensor that indicates when ambient humidity exceeds a preselected value, and when ambient humidity exceeds the preselected value, initiating the calibration. Another example may include initiating the calibration responsive to cabin temperature, or external air temperature, exceeding a preselected value. Yet another example may include initiating calibration responsive to a threshold duration of a defrost mode of the vehicle elapsing, or if a frequency of engaging defrost mode exceeds a predetermined frequency.

If, at 1405, conditions are not indicated to be met for conducting the interior humidity sensor compensation, method 1400 may proceed to 1410. At 1410, method 1400 may include maintaining current vehicle operating parameters. In other words, vehicle systems that rely on knowledge of interior humidity may remain unchanged. For example, a vehicle HVAC system (e.g. 175) may continue to use the value of intake humidity reported via the intake humidity sensor (e.g. 152), without the interior humidity sensor being compensated for. Method 1400 may then end.

Returning to 1405, responsive to conditions being indicated to be met for conducting the interior humidity sensor calibration, method 1400 may proceed to 1415. At 1415, method 1400 may include notifying the vehicle operator to initiate an interior humidity sensor calibration procedure. More specifically, the vehicle controller may send a wireless signal to a vehicle operator's personal computing device (e.g. 90), where said personal computing device may be equipped with a humidity sensor (e.g. 97), requesting initiation of the interior humidity sensor calibration. In other examples, the vehicle controller may additionally or alternatively display such a request on the vehicle's instrument panel (e.g. 196), which may in some examples be configured with a human machine interface (HMI), for displaying requests from the vehicle controller.

Subsequent to notifying the vehicle operator of the request to initiate calibration of the vehicle's interior humidity sensor, method 1400 may proceed to 1420. At 1420, method 1400 may include calibrating the interior humidity sensor via a software application on the personal computing device (e.g. 90). In some examples, calibrating the interior humidity sensor may include utilizing humidity data retrieved from one or more personal computing devices. Such a procedure will be discussed in detail below with regard to FIG. 15. Briefly, the method 1500 depicted below may comprise a sub-method of method 1400, which may enable the personal computing device(s) to provide an accurate estimation of vehicle interior humidity and provide said humidity estimation to the vehicle controller for compensating the interior humidity sensor (e.g. 152).

Turning now to FIG. 15, a high-level example method 1500 for utilizing one or more personal computing device(s) (e.g. 90) to compensate a vehicle's interior humidity sensor (e.g. 152), is shown. More specifically, method 1500 may comprise a sub-method of method 1400 depicted at FIG. 14. Method 1500 may include obtaining one or more accurate measurement(s) of vehicle interior humidity via a humidity sensor (e.g. 97) associated with the personal computing device (e.g. 90), and communicating the interior humidity measurement to the vehicle controller, such that the vehicle's interior humidity sensor (e.g. 152) may be compensated. In a case where more than one personal computing device is utilized to obtain the one or more humidity measurements, method 1500 may include increasing a confidence level associated with the one or more humidity measurements.

Method 1500 will be described with reference to the systems described herein and shown in FIGS. 1-5, though it should be understood that similar methods may be applied to other systems without departing from the scope of this disclosure. Method 1500 may be carried out by a controller, such as controller 12 in FIGS. 2-4, and may be stored at the controller as executable instructions in non-transitory memory. Instructions for carrying out method 1500 may be executed by the controller based on instructions stored on a memory of the controller and in conjunction with signals received from sensors of the vehicle system, such as the sensors described above with reference to FIGS. 1-5. The controller may employ vehicle system actuators, such as the actuators described above with reference to FIGS. 1-4, according to the method depicted below.

Method 1500 begins at 1505, and may include the vehicle controller sending a wireless signal to the personal computing device (e.g. 90), requesting the vehicle operator to position the personal computing device in a position within a threshold of the vehicle's interior humidity sensor (e.g. 152). In some examples, a camera (e.g. 98) associated with the personal computing device may be utilized to direct the vehicle operator to a location of the vehicle where the interior humidity sensor is positioned. As an example, the personal computing device (e.g. 90) may include a software application, which may enable communication between the vehicle controller and the personal computing device. The software application, in response to the request from the vehicle controller for the personal computing device to be positioned near the intake humidity sensor, may provide instructions that may be interpreted by the vehicle operator, to position the computing device near the interior humidity sensor. In some examples, said instructions may be audible, or may be provided on a display of the personal computing device, such that the vehicle operator may be instructed as to how to position the personal computing device in the vehicle. Positional information with regard to the personal computing device may be communicated wirelessly to the vehicle controller, for example.

Proceeding to step 1510, method 1500 may include indicating whether the personal computing device is in proper position (e.g. within the threshold distance from the interior humidity sensor). If, at 1510, the personal computing device is not in proper position, the vehicle controller may signal to the application that the personal computing device is not within the threshold distance of the interior humidity sensor, which may include the software application on the personal computing device providing additional instructions to the vehicle operator to properly position the personal computing device.

Alternatively, at 1510, responsive to an indication that the personal computing device is positioned within the threshold distance from the interior humidity sensor, method 1500 may proceed to 1515. At 1515, method 1500 may include retrieving humidity information from the personal computing device and interior humidity sensor (e.g. 152). More specifically, responsive to the personal computing device being positioned within the threshold distance from the interior humidity sensor, the personal computing device may initiate humidity measurement(s) via the humidity sensor (e.g. 97) for a duration (e.g. 10 seconds). While the personal computing device is determining the measurement(s) for humidity, the vehicle controller may additionally send a signal to the interior humidity sensor (e.g. 152), requesting humidity measurement(s) for a duration (e.g. 10 seconds). Data on humidity measured via the personal computing device (e.g. 90) may be communicated to the vehicle controller, and data from the vehicle controller may be communicated to the personal computing device. In other words, the software application may process both humidity data from the vehicle controller and from the personal computing device. In some examples, communication between the personal computing device and the vehicle controller may be established wirelessly, however it may be understood that in other examples, such information may be communicated via a USB connection, etc. In other words, one or more humidity measurements obtained with the one or more personal computing devices may be communicated wirelessly to the controller of the vehicle in some examples, whereas in other examples, the one or more humidity measurements obtained with the one or more personal devices may be communicated via wired communication (e.g. USB) to the vehicle controller.

With both the interior humidity determined via the personal computing device, as well as the interior humidity sensor, method 1500 may proceed to 1520. At 1520, method 1500 may include compensating the intake humidity sensor based on a comparison between the humidity measurement from the personal computing device and from the interior humidity sensor. For example, a gain or offset error may be determined as a function of the humidity measurement from the personal computing device, as compared to the interior humidity sensor (e.g. 152), such that the interior humidity sensor may be compensated.

While not explicitly illustrated, in some examples, more than one personal computing device may be utilized to obtain a number of measurements of humidity, such that a highest likelihood measurement may be indicated, where such a high likelihood measurement may be used to compensate the interior humidity sensor.

Thus, upon compensating the vehicle interior humidity sensor via data retrieved via the vehicle controller from one or more personal computing device(s), method 1500 may end.

Accordingly, returning to FIG. 14, after calibrating/compensating the vehicle's interior humidity sensor (e.g. 152), method 1400 may proceed to 1425. At 1425, method 1400 may include updating vehicle operating parameters relevant to the updated interior humidity sensor compensation. For example, accurate knowledge of interior humidity may enable precise control over environmental conditions inside the vehicle, by updating and/or adjusting operating parameters of a vehicle HVAC system (e.g. 175). Adjusting the heating, ventilation, and air conditioning system may include one or more of adjusting temperature blending in the cabin of the vehicle, adjusting a force or speed of one or more fan(s) configured to direct heated or cooled air to the cabin of the vehicle, adjusting operation of a clutch configured to regulate a compressor of an air conditioning system, and/or adjusting a heater shut-off valve to regulate a coolant flow to a heater core. Examples may include adjusting operation of a clutch (e.g. 210) that may regulate a compressor (e.g. 230) of an air conditioning system (e.g. 176), such that the interior of a vehicle cabin may be more precisely controlled. Other examples may include adjusting operation of an air conditioning system fan (e.g. 237), to more precisely control interior environmental conditions. In still other examples, at 1420, method 1400 may additionally or alternatively include controlling a heater shut-off valve (e.g. 322) such that coolant flow to a heater core (e.g. 90) may be regulated as a function of the compensated interior humidity sensor. In summary, any relevant parameter with regard to the vehicle's HVAC system (e.g. 175) may be adjusted/updated in order to more precisely regulate an interior environment of the vehicle, as a function of the compensated interior humidity sensor. Method 1400 may then end.

Thus, the methods of FIGS. 14-15 may enable a method comprising sending a request for a first humidity measurement from a controller of a vehicle to a personal computing device, the personal computing device equipped with a personal computing device humidity sensor. The method may include indicating when the personal computing device is within a threshold of an interior vehicle humidity sensor; receiving the first humidity measurement from the personal computing device in response to an indication that the personal computing device is within the threshold of the interior vehicle humidity sensor; indicating a second humidity measurement obtained from the interior vehicle humidity sensor; and correcting a gain or offset error of the interior vehicle humidity sensor based on a difference between the first humidity measurement from the personal computing device and the second humidity measurement obtained from the interior vehicle humidity sensor. In some examples, such a method may further comprise adjusting operation of a vehicle HVAC system in response to the correcting the gain or offset error of the interior vehicle humidity sensor. In some examples, adjusting operation of the vehicle HVAC system may further comprise adjusting temperature blending in the cabin of the vehicle, adjusting a force or speed of one or more fan(s) configured to direct heated or cooled air to the cabin of the vehicle, adjusting operation of a clutch configured to regulate a compressor of an air conditioning system, and/or adjusting a heater shut-off valve to regulate a coolant flow to a heater core.

The FIGS. 1-4, and the methods of FIGS. 14-15 may additionally enable a system for a vehicle comprising an interior vehicle humidity sensor positioned in a cabin of the vehicle, a vehicle climate control system, and a controller storing instructions in non-transitory memory that, when executed, cause the controller to indicate a first humidity measurement obtained via the interior vehicle humidity sensor. The controller may then receive a second humidity measurement from a personal computing device positioned inside the cabin of the vehicle within a predetermined threshold of the interior vehicle humidity sensor. The controller may then calibrate the interior vehicle humidity sensor as a function of the first humidity measurement and the second humidity measurement, and adjust one or more parameters of the vehicle climate control system in response to the calibrating of the interior vehicle humidity sensor.

In some examples, the controller may further comprise instructions to correct a gain or offset error of the interior vehicle humidity sensor based on the indicated first humidity measurement and the received second humidity measurement to calibrate the interior vehicle humidity sensor. In some examples, the vehicle climate control system may further comprise one or more fans configured to direct heated or cooled air to the cabin of the vehicle. The controller may further comprise instructions to adjust one or more parameters of the vehicle climate control system including adjusting a force or speed of the one or more fans responsive to calibrating the interior vehicle humidity sensor.

In some examples, the vehicle climate control system may further comprise a clutch configured to regulate an air conditioning compressor. The controller may further comprise instructions adjust operation of the clutch to regulate the air conditioning compressor responsive to calibrating the interior vehicle humidity sensor. In still further examples, the vehicle climate control system may further comprise a heater shut-off valve configured to regulate a coolant flow to a heater core of the vehicle. The controller may further comprise instructions to adjust the heater shut-off valve responsive to calibrating the interior vehicle humidity sensor, for example.

In this way, a vehicle interior humidity sensor may be regularly calibrated, or compensated. By regularly compensating the vehicle interior humidity sensor, operation of the HVAC system may be improved. Improved operation of the HVAC system may increase comfort of vehicle occupants, and may in some examples increase fuel economy.

The technical effect is to recognize that a humidity estimate or measurement exterior to the vehicle cabin may not always provide an accurate reflection of interior cabin humidity, and that in order to regularly compensate the interior humidity sensor, another method is desirable. Thus, the technical effect is to recognize that a personal computing device (e.g. cellular phone, laptop, etc.) equipped with a humidity sensor may be utilized to conduct a humidity measurement inside a cabin of the vehicle, where instructions as to how to obtain the humidity measurement may be stored on a software application running on the personal computing device. By compensating the interior humidity sensor via a personal computing device, where the personal computing device is capable of obtaining a humidity measurement in a close proximity to the interior humidity sensor, such a compensation may be robust and accurate as compared to a method where the interior humidity sensor may be calibrated based on an exterior humidity measurement, for example. By increasing accuracy and robustness of the interior humidity sensor calibration, HVAC system operation may be improved.

The systems described herein and with reference to FIGS. 1-4, along with the methods described herein, and with reference to FIGS. 14-15, may enable one or more systems and one or more methods. In one example, a method comprises calibrating a first vehicle humidity sensor positioned inside a cabin of a vehicle via obtaining one or more humidity measurements with one or more personal computing devices positioned inside the cabin; and adjusting a vehicle heating, ventilation, and air conditioning system responsive to calibrating the first vehicle humidity sensor. In a first example of the method, the method further includes wherein the one or more personal computing devices include a second humidity sensor. A second example of the method optionally includes the first example, and further includes wherein the one or more personal computing devices comprises a cellular phone. A third example of the method optionally includes any one or more or each of the first and second examples, and further includes wherein obtaining the one or more humidity measurements with the one or more personal computing devices further comprises positioning the one or more personal computing devices within a threshold distance from the first humidity sensor prior to obtaining the one or more humidity measurements. A fourth example of the method optionally includes any one or more or each of the first through third examples, and further includes wherein positioning the one or more personal computing devices within the threshold distance from the first humidity sensor includes using one or more cameras included in the one or more personal computing devices to direct the one or more personal computing devices to within the threshold distance. A fifth example of the method optionally includes any one or more or each of the first through fourth examples, and further includes wherein the one or more personal computing devices are equipped with a software application, the software application including instructions pertaining to how to obtain the one or more humidity measurements. A sixth example of the method optionally includes any one or more or each of the first through fifth examples, and further includes wherein the first vehicle humidity sensor is one of a dielectric or capacitive humidity sensor. A seventh example of the method optionally includes any one or more or each of the first through sixth examples, and further includes wherein the one or more humidity measurements obtained with the one or more personal computing devices are communicated wirelessly to a controller of the vehicle. An eighth example of the method optionally includes any one or more or each of the first through seventh examples, and further includes wherein the one or more humidity measurements obtained with the one or more personal computing devices are communicated via wired communication to a controller of the vehicle. A ninth example of the method optionally includes any one or more or each of the first through eighth examples, and further includes wherein calibrating the first vehicle humidity sensor includes correcting a gain or offset error of the first vehicle humidity sensor. A tenth example of the method optionally includes any one or more or each of the first through ninth examples, and further includes wherein adjusting the heating, ventilation, and air conditioning system includes one or more of adjusting temperature blending in the cabin of the vehicle, adjusting a force or speed of one or more fan(s) configured to direct heated or cooled air to the cabin of the vehicle, adjusting operation of a clutch configured to regulate a compressor of an air conditioning system, and/or adjusting a heater shut-off valve to regulate a coolant flow to a heater core. An eleventh example of the method optionally includes any one or more or each of the first through tenth examples, and further includes wherein obtaining one or more humidity measurements includes increasing a confidence level associated with the one or more humidity measurements in responsive to more than one humidity measurement being obtained via more than one personal computing device.

An example of a system for a vehicle comprises an interior vehicle humidity sensor positioned in a cabin of the vehicle; a vehicle climate control system; and a controller storing instructions in non-transitory memory that, when executed, cause the controller to: indicate a first humidity measurement obtained via the interior vehicle humidity sensor; receive a second humidity measurement from a personal computing device positioned inside the cabin of the vehicle within a predetermined threshold of the interior vehicle humidity sensor; calibrate the interior vehicle humidity sensor as a function of the first humidity measurement and the second humidity measurement; and adjust one or more parameters of the vehicle climate control system in response to the calibrating of the interior vehicle humidity sensor. In a first example of the system, the system further includes wherein the controller stores further instructions in non-transitory memory that, when executed, cause the controller to: correct a gain or offset error of the interior vehicle humidity sensor based on the indicated first humidity measurement and the received second humidity measurement to calibrate the interior vehicle humidity sensor. A second example of the system optionally includes the first example, and further includes wherein the vehicle climate control system further comprises: one or more fans configured to direct heated or cooled air to the cabin of the vehicle; and further comprising additional instructions in the non-transitory memory that, when executed, cause the controller to: adjust one or more parameters of the vehicle climate control system including adjusting a force or speed of the one or more fans responsive to calibrating the interior vehicle humidity sensor. A third example of the system optionally includes any one or more or each of the first and second examples, and further includes wherein the vehicle climate control system further comprises: a clutch configured to regulate an air conditioning compressor; and further comprising additional instructions in the non-transitory memory that, when executed, cause the controller to: adjust operation of the clutch to regulate the air conditioning compressor responsive to calibrating the interior vehicle humidity sensor. A fourth example of the system optionally includes any one or more or each of the first through third examples, and further includes wherein the vehicle climate control system further comprises: a heater shut-off valve configured to regulate a coolant flow to a heater core of the vehicle; and further comprising additional instructions in the non-transitory memory that, when executed, cause the controller to: adjust the heater shut-off valve responsive to calibrating the interior vehicle humidity sensor.

Another example of a method comprises sending a request for a first humidity measurement from a controller of a vehicle to a personal computing device, the personal computing device equipped with a personal computing device humidity sensor; indicating when the personal computing device is within a threshold of an interior vehicle humidity sensor; receiving the first humidity measurement from the personal computing device in response to an indication that the personal computing device is within the threshold of the interior vehicle humidity sensor; indicating a second humidity measurement obtained from the interior vehicle humidity sensor; and correcting a gain or offset error of the interior vehicle humidity sensor based on a difference between the first humidity measurement from the personal computing device and the second humidity measurement obtained from the interior vehicle humidity sensor. A first example of the method further comprises in response to the correcting the gain or offset error of the interior vehicle humidity sensor, adjusting operation of a vehicle heating, ventilation, and air conditioning system. A second example of the method optionally includes the first example, and further includes wherein adjusting operation of the vehicle heating, ventilation, and air conditioning system further comprises: adjusting temperature blending in the cabin of the vehicle, adjusting a force or speed of one or more fan(s) configured to direct heated or cooled air to the cabin of the vehicle, adjusting operation of a clutch configured to regulate a compressor of an air conditioning system, and/or adjusting a heater shut-off valve to regulate a coolant flow to a heater core.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
calibrating a first vehicle humidity sensor positioned inside a cabin of a vehicle via obtaining one or more humidity measurements with one or more personal computing devices positioned inside the cabin responsive to determining that the one or more personal computing devices are positioned within a threshold distance from the first vehicle humidity sensor; and
adjusting a vehicle heating, ventilation, and air conditioning system responsive to calibrating the first vehicle humidity sensor.

2. The method of claim 1, wherein the one or more personal computing devices include a second humidity sensor, and wherein calibrating the first vehicle humidity sensor comprises calibrating the first vehicle humidity sensor based on a comparison between a first humidity measurement obtained from the first vehicle humidity sensor and a second humidity measurement obtained from the second humidity sensor.

3. The method of claim 1, wherein the one or more personal computing devices comprises a cellular phone.

4. The method of claim 1, wherein determining that the one or more personal computing devices are within the threshold distance from the first vehicle humidity sensor includes determining that the one or more personal computing devices are within the threshold distance based on output from one or more cameras included in the one or more personal computing devices.

5. The method of claim 1, wherein the one or more personal computing devices are equipped with a software application, the software application including instructions pertaining to how to obtain the one or more humidity measurements.

6. The method of claim 1, wherein the first vehicle humidity sensor is one of a dielectric or capacitive humidity sensor.

7. The method of claim 1, wherein a controller of the vehicle is configured to wirelessly communicate with the one or more personal computing devices to obtain the one or more humidity measurements.

8. The method of claim 1, wherein a controller of the vehicle is configured to communicate with the one or more personal computing devices via a wired connection to obtain the one or more humidity measurements.

9. The method of claim 2, wherein calibrating the first vehicle humidity sensor includes correcting a gain or offset error of the first vehicle humidity sensor based on the comparison.

10. The method of claim 1, wherein adjusting the heating, ventilation, and air conditioning system includes one or more of adjusting temperature blending in the cabin of the vehicle, adjusting a force or speed of one or more fan(s) configured to direct heated or cooled air to the cabin of the vehicle, adjusting operation of a clutch configured to regulate a compressor of an air conditioning system, and/or adjusting a heater shut-off valve to regulate a coolant flow to a heater core.

11. The method of claim 1, wherein obtaining the one or more humidity measurements includes increasing a confidence level associated with the one or more humidity measurements in response to more than one humidity measurement being obtained via more than one personal computing device.

12. A system for a vehicle, comprising:
an interior vehicle humidity sensor positioned in a cabin of the vehicle;
a vehicle climate control system; and
a controller storing instructions in non-transitory memory that, when executed, cause the controller to:
obtain a first humidity measurement via the interior vehicle humidity sensor;
receive a second humidity measurement from a personal computing device positioned inside the cabin of the vehicle within a predetermined threshold of the interior vehicle humidity sensor;
calibrate the interior vehicle humidity sensor as a function of the first humidity measurement and the second humidity measurement; and
adjust one or more parameters of the vehicle climate control system in response to the calibrating of the interior vehicle humidity sensor.

13. The system of claim 12, wherein the controller stores further instructions in non-transitory memory that, when executed, cause the controller to:
correct a gain or offset error of the interior vehicle humidity sensor based on the indicated first humidity measurement and the received second humidity measurement to calibrate the interior vehicle humidity sensor.

14. The system of claim 12, wherein the vehicle climate control system further comprises:
one or more fans configured to direct heated or cooled air to the cabin of the vehicle; and
further comprising additional instructions in the non-transitory memory that, when executed, cause the controller to:
adjust one or more parameters of the vehicle climate control system including adjusting a force or speed of the one or more fans responsive to calibrating the interior vehicle humidity sensor.

15. The system of claim 12, wherein the vehicle climate control system further comprises:
a clutch configured to regulate an air conditioning compressor; and
further comprising additional instructions in the non-transitory memory that, when executed, cause the controller to:
adjust operation of the clutch to regulate the air conditioning compressor responsive to calibrating the interior vehicle humidity sensor.

16. The system of claim 12, wherein the vehicle climate control system further comprises:
a heater shut-off valve configured to regulate a coolant flow to a heater core of the vehicle; and
further comprising additional instructions in the non-transitory memory that, when executed, cause the controller to:
adjust the heater shut-off valve responsive to calibrating the interior vehicle humidity sensor.

17. A method for a vehicle, comprising:
sending a request for a first humidity measurement from a controller of a vehicle to a personal computing device, the personal computing device equipped with a personal computing device humidity sensor;
indicating when the personal computing device is within a threshold distance of an interior vehicle humidity sensor;
receiving the first humidity measurement from the personal computing device in response to an indication that the personal computing device is within the threshold distance of the interior vehicle humidity sensor;
obtaining a second humidity measurement from the interior vehicle humidity sensor; and
correcting a gain or offset error of the interior vehicle humidity sensor based on a difference between the first humidity measurement from the personal computing device and the second humidity measurement obtained from the interior vehicle humidity sensor.

18. The method of claim 17, further comprising:
in response to the correcting the gain or offset error of the interior vehicle humidity sensor, adjusting operation of a vehicle heating, ventilation, and air conditioning system.

19. The method of claim 18, wherein adjusting operation of the vehicle heating, ventilation, and air conditioning system further comprises one or more of:
adjusting temperature blending in a cabin of the vehicle, adjusting a force or speed of one or more fan(s) configured to direct heated or cooled air to the cabin of the vehicle, adjusting operation of a clutch configured to regulate a compressor of the air conditioning system, or adjusting a heater shut-off valve to regulate a coolant flow to a heater core.

* * * * *